(12) United States Patent
Stevenson et al.

(10) Patent No.: US 8,694,102 B2
(45) Date of Patent: Apr. 8, 2014

(54) IONIZING RADIATION-PROTECTED ACTIVE IMPLANTABLE MEDICAL DEVICE

(75) Inventors: Ryan A. Stevenson, Maple Valley, WA (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/367,501

(22) Filed: Feb. 7, 2012

(65) Prior Publication Data

US 2012/0230003 A1    Sep. 13, 2012

Related U.S. Application Data

(60) Provisional application No. 61/450,873, filed on Mar. 9, 2011.

(51) Int. Cl.
*A61N 1/00* (2006.01)
*H05K 9/00* (2006.01)

(52) U.S. Cl.
USPC ............................................. 607/36; 361/816

(58) Field of Classification Search
USPC ........ 607/1, 4–5, 116; 600/508–528; 361/816
See application file for complete search history.

(56) References Cited

U.S. PATENT DOCUMENTS

| | | | |
|---|---|---|---|
| 5,998,867 A * | 12/1999 | Jensen et al. | 257/729 |
| 6,238,340 B1 * | 5/2001 | Alt et al. | 600/431 |
| 6,262,362 B1 * | 7/2001 | Czjakowski et al. | 174/360 |
| 2003/0014082 A1 * | 1/2003 | Schu et al. | 607/5 |
| 2006/0259093 A1 * | 11/2006 | Stevenson et al. | 607/37 |
| 2009/0036944 A1 * | 2/2009 | Fonte | 607/36 |
| 2009/0243756 A1 * | 10/2009 | Stevenson et al. | 333/172 |
| 2009/0299289 A1 * | 12/2009 | Kamen et al. | 604/151 |
| 2011/0054582 A1 * | 3/2011 | Dabney et al. | 607/116 |
| 2011/0102967 A1 * | 5/2011 | Munns et al. | 361/302 |
| 2011/0112615 A1 * | 5/2011 | Hoegh et al. | 607/116 |
| 2012/0219100 A1 * | 8/2012 | Lagunas-Solar et al. | 376/189 |

OTHER PUBLICATIONS

Helenstine, T., "Periodic Table of the Elements Density". About Chemistry, 2010.*
Periodic Table of the Elements from the 58th edition of the CRC Handbook of Chemisty and Physics, 1977.*

* cited by examiner

*Primary Examiner* — Catherine Voorhees
(74) *Attorney, Agent, or Firm* — Michael F. Scalise

(57) ABSTRACT

A radiation protected active implantable medical device includes an ionizing radiation shield disposed over at least one major surface of an electronics package, a microprocessor, or both contained within an AIMD housing. The ionizing radiation shield is made from a high atomic number, high atomic weight, high density material such as led, gold, platinum, iridium, tungsten or tantalum and has an atomic weight of at least 180 and a density of at least 11 grams per cubic centimeter. The ionizing radiation shield has a thickness of at least 0.25 millimeters and is preferably no thicker than 1.05 millimeters and has an overall attenuation of ionizing radiation of at least 0.5 HVL.

46 Claims, 19 Drawing Sheets

Linear attenuation coefficient of water and the contribution of each interaction to the total attenuation of X rays as a function of the energy.

| Half Value Layer Thickness at 150 KeV (mm) | | | |
|---|---|---|---|
| Material | 1st HVL | 2nd HVL | 3rd HVL |
| Adipose | 281.39 | 562.78 | 844.17 |
| Skeletal Muscle | 238.22 | 476.44 | 714.66 |
| Aluminum | 87.57 | 175.13 | 262.70 |
| Titanium | 28.52 | 57.05 | 85.57 |
| Lead | 0.58 | 1.16 | 1.73 |
| Gold | 0.35 | 0.70 | 1.05 |
|  | 50% | 25% | 12.5% |

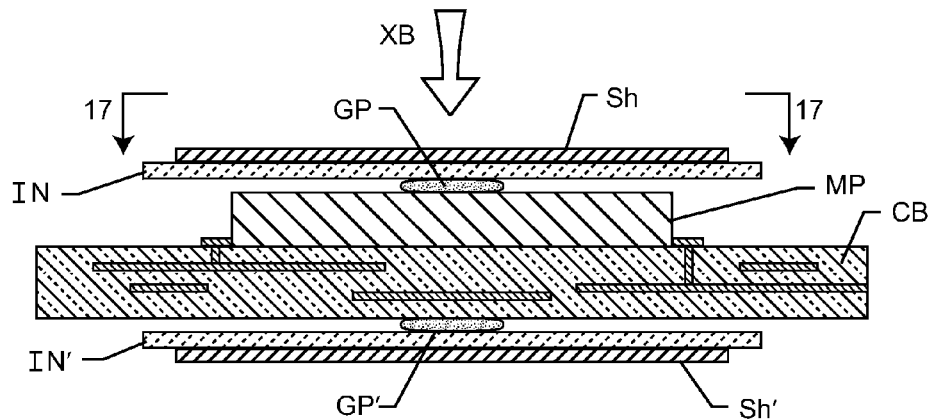
FIG. 14
| Atomic Number | Atomic Weight | Symbol | Name | Density (g/cm^3) |
|---|---|---|---|---|
| 73 | 180.9 | Ta | Tantalum | 16.65 |
| 74 | 183.9 | W | Tungsten | 19.3 |
| 77 | 192.2 | Ir | Iridium | 22.42 |
| 78 | 195.1 | Pt | Platinum | 21.45 |
| 79 | 196.9 | Au | Gold | 19.32 |
| 82 | 207.2 | Pb | Lead | 11.35 |
FIG. 15
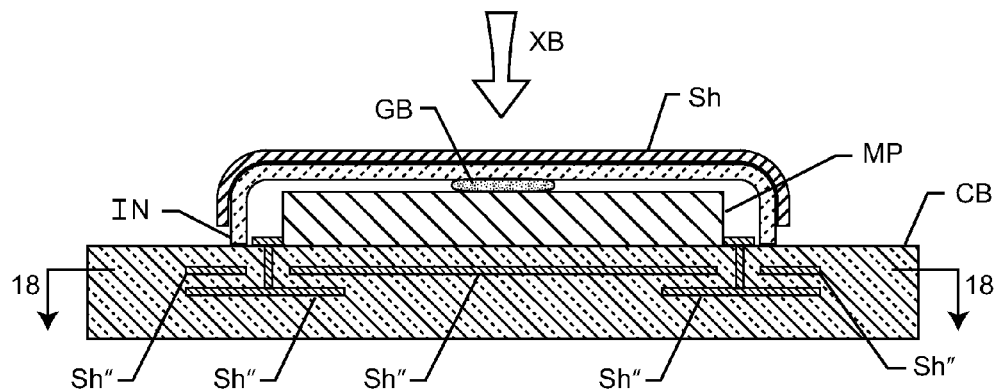
FIG. 16

IONIZING RADIATION-PROTECTED ACTIVE IMPLANTABLE MEDICAL DEVICE

FIELD OF INVENTION

This invention relates to protecting active implantable medical devices (AIMDs) from the undesirable effects that can be associated with ionizing radiation. In particular, the present invention provides high atomic number and high density shielding adjacent to sensitive electronic circuits, such as microprocessors and memory circuits.

BACKGROUND OF THE INVENTION

Since its introduction in the 1970s, computed tomography (CT) has become an important tool in medical imaging to supplement X-rays and medical ultrasonography. It has more recently been used for preventive medicine or screening for disease, for example, CT colonography for patients with a high risk of colon cancer, or full-motion heart scans for patients with high risk of heart disease. A number of institutions offer full-body scans for the general population. However, this is a controversial practice, given its lack of proven benefit, its cost, the radiation exposure to the patient, and the risk of finding 'incidental' abnormalities that may trigger additional investigations.

CT scanning of the head is typically used to detect infarction, tumors, calcifications, hemorrhage and bone trauma. Of the above, hypodense (dark) structures indicate infarction and tumors, hyperdense (bright) structures indicate calcifications and hemorrhage, and bone trauma can be seen as disjunction in bone windows.

CT can be used for detecting both acute and chronic changes in the lung parenchyma, that is, the internals of the lungs. It is particularly relevant here because normal two dimensional x-rays do not show such defects. A variety of different techniques are used depending on the suspected abnormality. For evaluation of chronic interstitial processes (emphysema, fibrosis, and so forth), thin sections with high spatial frequency reconstructions are used—often scans are performed both in inspiration and expiration. This special technique is called High Resolution CT (HRCT). HRCT is normally done within thin slices with skipped areas between the thin slices. Therefore it produces a sampling of the lung and not continuous images. Continuous images are provided in a standard CT of the chest.

CT angiography (CTA) of the chest is also becoming the primary method for detecting pulmonary embolism (PE) and aortic dissection, and requires accurately timed rapid injections of contrast (Bolus Tracking) and high-speed helical scanners. CT is the standard method of evaluating abnormalities seen on chest X-ray and of following findings of uncertain acute significance. Cardiac CTA is now being used to diagnose coronary artery disease.

CT pulmonary angiogram (CTPA) is a medical diagnostic test used to diagnose pulmonary embolism (PE). It employs computed tomography to obtain an image of the pulmonary arteries. MDCT (multi detector CT) scanners give the optimum resolution and image quality for this test. Images are usually taken on a 0.625 mm slice thickness, although 2 mm is sufficient. 50-100 ml/s of contrast is given to the patient at the rate of 4 ml/s. The tracker/locator is placed at the level of the pulmonary arteries, which sit roughly at the level of the carina. Images are acquired with the maximum intensity of radio-opaque contrast in the pulmonary arteries. This is done using bolus tracking. CT machines are now so sophisticated that the test can be done with a patient visit of 5 minutes with an approximate scan time of only 5 seconds or less.

With the advent of subsecond rotation combined with multi-slice CT (up to 320-slices), high resolution and high speed can be obtained at the same time, allowing excellent imaging of the coronary arteries (cardiac CT angiography). Images with an even higher temporal resolution can be formed using retrospective ECG gating. In this technique, each portion of the heart is imaged more than once while an ECG trace is recorded. The ECG is then used to correlate the CT data with their corresponding phases of cardiac contraction. Once this correlation is complete, all data that were recorded while the heart was in motion (systole) can be ignored and images can be made from the remaining data that happened to be acquired while the heart was at rest (diastole). In this way, individual frames in a cardiac CT investigation have a better temporal resolution than the shortest tube rotation time.

Because the heart is effectively imaged more than once (as described above), cardiac CT angiography results in a relatively high radiation exposure, around 12 milliSievert ("mSv"). Currently, newer acquisition protocols have been developed drastically reducing the X-rays radiation exposure, down to 1 mSv (cfr. Pavone, Fioranelli, Dowe: Computed Tomography on Coronary Arteries, Springer 2009). For the sake of comparison, a chest X-ray carries a dose of approximately 0.02 to 0.2 mSv and natural background radiation exposure is around 0.01 mSv/day. Thus, cardiac CTA is equivalent to approximately 100-600 chest X-rays or over 3 years worth of natural background radiation.

Dual Source CT scanners, introduced in 2005, allow higher temporal resolution by acquiring a full CT slice in only half a rotation, thus reducing motion blurring at high heart rates and potentially allowing for shorter breath-hold time. This is particularly useful for ill patients who have difficulty holding their breath or who are unable to take heart-rate lowering medication.

The speed advantages of 64-slice MSCT have rapidly established it as the minimum standard for newly installed CT scanners intended for cardiac scanning. Manufacturers have developed 320-slice and true 'volumetric' scanners, primarily for their improved cardiac scanning performance.

The latest MSCT scanners acquire images only at 70-80% of the R-R interval (late diastole). This prospective gating can reduce effective dose from 10-15 mSv to as little as 1.2 mSv in follow-up patients acquiring at 75% of the R-R interval. Effective doses with well trained staff doing coronary imaging can average less than the doses for conventional coronary angiography.

CT is a sensitive method for diagnosis of abdominal diseases. It is used frequently to determine stage of cancer and to follow progress. It is also a useful test to investigate acute abdominal pain (especially of the lower quadrants, whereas ultrasound is the preferred first line investigation for right upper quadrant pain). Renal stones, appendicitis, pancreatitis, diverticulitis, abdominal aortic aneurysm, and bowel obstruction are conditions that are readily diagnosed and assessed with CT. CT is also the first line for detecting solid organ injury after trauma.

Multidetector CT (MDCT) can clearly delineate anatomic structures in the abdomen, which is critical in the diagnosis of internal diaphragmatic and other nonpalpable or unsuspected hernias. MDCT also offers clear detail of the abdominal wall allowing wall hernias to be identified accurately. CT is often used to image complex fractures, especially ones around joints, because of its ability to reconstruct the area of interest in multiple planes. Fractures, ligamentous injuries and dislocations can easily be recognized with a 0.2 mm resolution.

There are several advantages that CT has over traditional 2D medical radiography. First, CT completely eliminates the superimposition of images of structures outside the area of interest. Second, because of the inherent high-contrast resolution of CT, differences between tissues that differ in physical density by less than 1% can be distinguished. Finally, data from a single CT imaging procedure consisting of either multiple contiguous or one helical scan can be viewed as images in the axial, coronal, or sagittal planes, depending on the diagnostic task. This is referred to as multiplanar reformatted imaging.

CT is regarded as a moderate to high radiation diagnostic technique. While technical advances have improved radiation efficiency, there has been simultaneous pressure to obtain higher-resolution imaging and use more complex scan techniques, both of which require higher doses of radiation. The improved resolution of CT has permitted the development of new investigations, which may have advantages; compared to conventional angiography for example, CT angiography avoids the invasive insertion of an arterial catheter and guide wire; CT colonography (also known as virtual colonoscopy or VC for short) may be as useful as a barium enema for detection of tumors, but may use a lower radiation dose. VC is increasingly being used as a diagnostic test for bowel cancer and can negate the need for a colonoscopy.

The greatly increased availability of CT, together with its value for an increasing number of conditions, has been responsible for a large rise in popularity. So large has been this rise that, in the most recent comprehensive survey in the United Kingdom, CT scans constituted 7% of all radiologic examinations.

The radiation dose for a particular study depends on multiple factors: volume scanned, patient build, number and type of scan sequences, and desired resolution and image quality. Additionally, two helical CT scanning parameters—tube current and pitch—can be adjusted easily and have a profound effect on radiation dose.

| Examination | Typical effective dose (mSv) | (millirem) |
| --- | --- | --- |
| Chest X-ray | 0.1 | 10 |
| Head CT | 1.5 | 150 |
| Screening mammography | 3 | 300 |
| Abdomen CT | 5.3 | 530 |
| Chest CT | 5.8 | 580 |
| CT colonography (virtual colonoscopy) | 3.6-8.8 | 360-880 |
| Chest, abdomen and pelvis CT | 9.9 | 990 |
| Cardiac CT angiogram | 6.7-13 | 670-1300 |
| Barium enema | 15 | 1500 |
| Neonatal abdominal CT | 20 | 2000 |

From the foregoing, it will be appreciated that CT scanning is growing in popularity and is being used to image human tissues literally all over the body. The inventors view the recent reports of energetic X-rays from CT scans as being the "tip of an iceberg." That is fast CT scans are increasingly being used for thoracic imaging where cardiac pacemakers are typically implanted. However, AIMDs are increasingly being implanted all over the human body as well. Accordingly, the chance for energetic X-ray from either diagnostic or therapeutic devices being imaged directly onto an AIMD is increasing and will continue to increase in the future.

X-ray slice data is generated using an X-ray source that rotates around the object; X-ray sensors are positioned on the opposite side of the circle of rotation from the X-ray source. The earliest sensors were scintillation detectors, with photomultiplier tubes excited by (typically) cesium iodide crystals. Cesium iodide was replaced during the 1980s by ion chambers containing high pressure Xenon gas. These systems were in turn replaced by scintillation systems based on photo diodes instead of photomultipliers and modern scintillation materials with more desirable characteristics. Many data scans are progressively taken as the object is gradually passed through the gantry.

Newer machines with faster computer systems and newer software strategies can process not only individual cross-sections but continuously changing cross-sections as the gantry, with the object to be imaged, is slowly and smoothly slid through the X-ray circle. These are called helical or spiral CT machines. Their computer systems integrate the data of the moving individual slices to generate three-dimensional volumetric information (3D-CT scan), in turn viewable from multiple different perspectives on attached CT workstation monitors. This type of data acquisition requires enormous processing power, as the data are arriving in a continuous stream and must be processed in real-time.

In conventional CT machines, an X-ray tube and detector are physically rotated behind a circular shroud (FIGS. 1-4); in electron beam tomography (EBT) the tube is far larger and higher power to support the high temporal resolution. The electron beam is deflected in a hollow funnel-shaped vacuum chamber. X-rays are generated when the beam hits the stationary target. The detector is also stationary. This arrangement can result in very fast scans, but is extremely expensive.

Once the scan data has been acquired, the data must be processed using a form of tomographic reconstruction, which produces a series of cross-sectional images. The most common technique in general use is filtered back projection, which is straight-forward to implement and can be computed rapidly. Mathematically, this method is based on the Radon transform. However, this is not the only technique available: the original EMI scanner solved the tomographic reconstruction problem by linear algebra, but this approach was limited by its high computational complexity, especially given the computer technology available at the time. More recently, manufacturers have developed iterative physical model-based expectation-maximization techniques. These techniques are advantageous because they use an internal model of the scanner's physical properties and of the physical laws of X-ray interactions. By contrast, earlier methods have assumed a perfect scanner and highly simplified physics, which leads to a number of artifacts and reduced resolution—the result is images with improved resolution, reduced noise and fewer artifacts, as well as the ability to greatly reduce the radiation dose in certain circumstances. The disadvantage is a very high computational requirement, which is at the limits of practicality for current scan protocols.

Pixels in an image obtained by CT scanning are displayed in terms of relative radiodensity. The pixel itself is displayed according to the mean attenuation of the tissue(s) that the pixel corresponds to on a scale from +3071 (most attenuating) to −1024 (least attenuating) on the Hounsfield scale. A pixel is a two dimensional image unit (picture element—pixel) based on the matrix size and the field of view. When the CT slice thickness is also factored in, the unit is known as a Voxel, which is a three dimensional unit. The phenomenon that one part of the detector cannot differentiate between different tissues is called the "Partial Volume Effect". That means that a large amount of cartilage and a thin layer of compact bone can cause the same attenuation in a voxel as hyperdense cartilage alone. Water has an attenuation of 0 Hounsfield units (HU) while air is −1000 HU, cancellous bone is typically +400 HU, cranial bone can reach 2000 HU or more (os temporale) and can cause artifacts. The attenuation of metallic implants depends on the atomic number of the element used: titanium usually has an amount of +1000 HU, iron steel can completely extinguish the X-ray and is therefore responsible for well-known line-artifacts in computed tomograms. Artifacts are caused by abrupt transitions between low and high-density materials, which results in data values that exceed the dynamic range of the processing electronics.

Because contemporary CT scanners offer isotropic or near isotropic, resolution, display of images does not need to be restricted to the conventional axial images. Instead, it is possible for a software program to build a volume by "stacking" the individual slices one on top of the other. The program may then display the volume in an alternative manner.

Multiplanar reconstruction (MPR) is the simplest method of reconstruction. A volume is built by stacking the axial slices. The software then cuts slices through the volume in a different plane (usually orthogonal). Optionally, a special projection method, such as maximum-intensity projection (MIP) or minimum-intensity projection (mIP), can be used to build the reconstructed slices.

MPR is frequently used for examining the spine. Axial images through the spine will only show one vertebral body at a time and cannot reliably show the intervertebral discs. By reformatting the volume, it becomes much easier to visualize the position of one vertebral body in relation to the others.

Modern software allows reconstruction in non-orthogonal (oblique) planes so that the optimal plane can be chosen to display an anatomical structure. This may be particularly useful for visualizing the structure of the bronchi as these do not lie orthogonal to the direction of the scan.

For vascular imaging, curved-plane reconstruction can be performed. This allows bends in a vessel to be "straightened" so that the entire length can be visualized on one image, or a short series of images. Once a vessel has been "straightened" in this way, quantitative measurements of length and cross sectional area can be made, so that surgery or interventional treatment can be planned.

MPR reconstructions enhance areas of high radiodensity, and so are useful for angiographic studies. MPR reconstructions tend to enhance air spaces so are useful for assessing lung structure.

Surface rendering: a threshold value of radiodensity is set by the operator (e.g. a level that corresponds to bone). From this, a three-dimensional model can be constructed using edge detection image processing algorithms and displayed on screen. Multiple models can be constructed from various different thresholds, allowing different colors to represent each anatomical component such as bone, muscle, and cartilage. However, the interior structure of each element is not visible in this mode of operation.

Volume rendering: Surface rendering is limited in that it will only display surfaces which meet a threshold density, and will only display the surface that is closest to the imaginary viewer. In volume rendering, transparency and colors are used to allow a better representation of the volume to be shown in a single image—e.g. the bones of the pelvis could be displayed as semi-transparent, so that even at an oblique angle, one part of the image does not conceal another.

As previously mentioned, there have been a number of recent reports of X-ray radiation causing interference in implantable cardiac pacemakers.

Reference 1 X-RAY RADIATION CAUSES ELECTROMAGNETIC INTERFERENCE IN IMPLANTABLE CARDIAC PACEMAKERS, Minour Hirose, Ph.D., Keiichi Tachikawa, C.C.E., Masanori Ozaki, R.T., Naoki Umezawa, R.T., Toshihiro Shinbo, C.C.E., Kenichi Kokubo, Ph.D., and Hirosuke Kobayashi, M.D., Ph.D., from the Department of Medical Engineering and Technology, School of Allied Health Services, Kitasato University, Kanagawa, Japan; Department of Clinical Engineering, Jichi Medical University Hospital, Tochigi, Japan; and Department of Radiological Technology, School of Allied Health Sciences, Kitasato University, Kanagawa, Japan, PACE, Vol. 33, October 2010, No. 1174. The conclusion was that "X-ray radiation caused interference in some implantable cardiac pacemakers, probably because the CMOS (microelectronic) component was irradiated. The occurence of EMI depended on the pacemaker model, sensing threshold of the pacemaker, and X-ray radiation conditions, PACE 2010; 1174-1181."

Reference 2 "RADIATION THERAPY IN ONCOLOGY PATIENTS WHO HAVE A PACEMAKER OR IMPLANTABLE CARDIOVERTER-DEFIBRILLATOR," Bart Frizzell, MD, Department of Radiation Oncology, Wake Forest University, Winston-Salem, N.C., and Department of Radiation Oncology, High Point Regional Cancer Center, High Point, N.C., Technology, Community Oncology, October 2009, Volume 6/Number 10.

Reference 3 On Jul. 14, 2008, the FDA released a warning. FDA PRELIMINARY PUBLIC HEALTH NOTIFICATION: POSSIBLE MALFUNCTION OF ELECTRONIC MEDICAL DEVICES CAUSED BY COMPUTED TOMOGRAPHY (CT) SCANNING, Date Jul. 14, 2008. This FDA public health notification is available on the Internet at http://www.fda.gov/cdrh/safety.html. Questions about the FDA notification can be answered at the Office of Surveillance and Biometrics (HFZ-520), 1350 Piccard Drive, Rockville, Md., 20850.

Also cited in the FDA article are references 4, 5 and 6 listed below:

Reference 4 "DOES HIGH-POWER COMPUTED TOMOGRAPHY SCANNING EQUIPMENT AFFECT THE OPERATION OF PACEMAKERS?," Yamaji, S., et al., Circulation Journal 70:190-197 (2006).

Reference 5 "EFFECTS OF CT IRRADIATION ON IMPLANTABLE CARDIAC RHYTHM MANAGEMENT DEVICES," McCollough, C., et al., Radiology 243 (3):766-774 (2007).

Reference 6 "HAZARD REPORT—CT SCANS CAN AFFECT THE OPERATION OF IMPLANTED ELECTRONIC DEVICES," ECRI Institute Problem Reporting System, Health Devices 36 (4):136-138 (2007).

Additional references include:

Reference 7 "DOES HIGH-POWER COMPUTED TOMOGRAPHY SCANNING EQUIPMENT AFFECT THE OPERATION OF PACEMAKERS?", Satoshi Yamaji, MD; Shinobu Imai, MD; Funio Saito, MD; Hiroshi Yagi, MD; Toshio Kushiro, MD; Takahisa Uchiyama, MD, Circulation Journal, Volume 70, February 2006. "Conclusions: Malfunctions of the pacemaker during CT may be caused by diagnostic radiant rays and although they are transient, the possibility of lethal arrhythmia cannot be ignored. (Circ J 2006; 70:190-197)."

Reference 8 "EFFECTS OF CT IRRADIATION ON IMPLANTABLE CARDIAC RHYTHM MANAGEMENT DEVICES," Cynthia H. McCollough, PhD; Jie Zhang, PhD; Andrew N. Primak, PhD; Wesley J. Clement, BSEE; John R. Buysman, PhD, from the Department of Radiology, Mayo Clinic College of Medicine, 200 First St. SW, Rochester, Minn., 55905 (C.H.M., J.Z., A.N.P.); and Cardiac Rhythm Disease Management, Medtronic, Minneapolis, Minn. (W.J.C., J.R.B.). Received Jun. 8, 2006; revision requested August 10; revision received November 21; final version accepted December 6. Address correspondence to C.H.M. (email: mccollough.cynthis@mayo.edu), Radiology: Volume 243: Number 3—June 2007. In this article, 13 pacemaker models and 8 ICD models were exposed to ionizing radiation from both spiral and dynamic CT at maximum typical dose levels. Two different CT systems were chosen to represent current state-of-the-art technology: a 16-channel system (LightSpeed 16; GE Healthcare, Waukesha, Wis. and a 64-channel system (Sensation 64; Siemens Medical Solutions, Forchheim, Germany). The study revealed that ionizing radiation from CT examinations can indeed influence implantable device operation. The effects included over-sensing (inhibition), tracking, and safety pacing, and partial electrical reset (PER). The effects observed were associated with the direct radiation of the AIMD housing (electronics module). No device in this particular study was permanently damaged.

There have been a number of recent reports and publications that high-dose-rate computed tomography (CT scanners) can interfere with cardiac pacemakers or ICDs. X-ray computed tomography or CT is a medical imaging modality employing computer processing to reconstruct two- or three-dimensional images from the transmission of X-rays through the body. Digital geometry processing is used to generate a three-dimensional image of the inside of an object from a large series of two-dimensional X-ray images taken around a single axis of rotation.

CT produces a volume of data which can be manipulated, through a process known as "windowing," in order to demonstrate various bodily structures based on their ability to block the X-ray beam. Although historically the images generated were in the axial or transverse plane, orthogonal to the long axis of the body, modern scanners allow this volume of data to be reformatted in various planes or even as volumetric (3D) representations of structures.

Usage of CT has increased dramatically over the last two decades. An estimated 72 million scans were performed in the United States in 2007.

Recently, CT scanners have evolved to operate at increasingly higher dose rates. Experience by NASA in space radiation environments has demonstrated that microcircuits and/or electronic chips can be affected by various forms of radiation including high-energy photons (e.g. X-rays and Gamma rays), and particles such as energetic protons. NASA has solved these problems by bulky radiation shields, such as shields made of light weight material such as aluminum. In addition to or in lieu of shielding, NASA engineers and their subcontractors have also engineered radiation hardened (rad-hard) chip sets. Rad-hard chipsets can be realized either through circuit design techniques (rad-hard by design) or through materials engineering. Rad-hard by design consists of approaches such as triple modular redundancy (TMR). For example, in a microelectronic chip there could be three redundant parallel gates. The voting process entails the following logic: if gate 1 was giving an indication of a one and gates 2 and 3 were giving an indication of zero, then a zero would be voted on/selected. Probability and statistics have indicated that the likelihood of two or more gates being affected by a radiation bit flip at the same time is extremely unlikely.

Unfortunately, when considering active implantable medical devices, all of these prior art methods have several problems associated with them. In order for aluminum or other low-cost light-weight materials to be used as an effective shield, they need to be relatively thick because of their low densities and low atomic numbers. These thicknesses are far too thick to be of any practical benefit for use in an active implantable medical device. In addition, AIMDs such as cardiac pacemakers have evolved to be very small in size. Using a redundant rad-hard gate voting technique would more than double (potentially triple) the size of the chip set. There is simply not enough room in a modern cardiac pacemaker to accomplish this. To fully understand the issues, one needs to also understand the evolution of X-ray sources as used in medical diagnostic procedures such as CT scans. Not only have pacemakers been evolving to be much smaller, these X-ray sources have been evolving so that they are now operating at much higher dose rates and energies than ever before.

Accordingly, there is a need for radiation shielding for active implantable medical devices that meets the requirements of being lightweight, volumetrically efficient, and of reasonable cost. This type of shielding is not satisfied by traditional approaches such as the lead vest worn by X-ray technicians. Such shields are way too bulky and heavy.

SUMMARY OF THE INVENTION

The present invention is directed to an ionizing radiation-protected active implantable medical device (AIMD). The device comprises an AIMD housing containing an electronics package that includes a microprocessor. An ionizing radiation shield is disposed over at least one major surface of the electronics package, the microprocessor, or both. The ionizing radiation shield may include a plurality of shields that substantially surround the electronics package, the microprocessor, or both. The ionizing radiation shield may be attached to the electronics package, the microprocessor, or both.

The ionizing radiation shield may include an electrically insulated substrate adjacent to the electronics package, the microprocessor, or both, and a high density shield material opposite the electronics package, the microprocessor, or both relative to the electrically insulated substrate. The ionizing radiation shield may also be disposed over a plurality of major surfaces of the electronics package, the microprocessor, or both. The electronics package may include a circuit board, wherein the ionizing radiation shield is disposed within the circuit board.

The AIMD preferably comprises a cochlear implant, a piezoelectric sound bridge transducer, a neurostimulator, a brain stimulator, a cardiac pacemaker, a left ventricular assist device, an artificial heart, a drug pump, a bone growth stimulator, a urinary incontinence device, a pain relief spinal cord stimulator, an anti-tremor stimulator, an implantable cardioverter defibrillator, or a congestive heart failure device.

The ionizing radiation shield may also be a high density liner disposed adjacent to an interior surface of the AIMD housing. The housing liner may be plated over a substantial portion of the interior surface of the AIMD housing. Alternatively, the ionizing radiation shield may be disposed over a limited portion of the interior surface of the AIMD housing immediately adjacent to the electronics package, the microprocessor, or both. The AIMD housing may include an interior recess in which the ionizing radiation shield is disposed.

Preferably, the ionizing radiation shield has a thickness of at least 0.25 millimeters. The ionizing radiation shield may comprise a high atomic number insert in the AIMD housing adjacent to the electronics package, the microprocessor, or both. The high atomic number insert may comprise a biocompatible substrate and a high atomic number and high density shield material co-bonded to the substrate and disposed within the AIMD housing.

The ionizing radiation shield may be comprised of material selected from the group consisting of led, gold, platinum, iridium, tungsten and tantalum. Preferably, the ionizing radiation shield is comprised of gold and has a thickness of between 0.25 millimeters and 1.05 millimeters. The ionizing radiation shield preferably has an overall attenuation of ionizing radiation of at least 0.5 HVL. Preferably, the ionizing radiation shield has an atomic weight of at least one hundred eighty and a density of at least eleven grams per cubic centimeter.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 14 is an enlarged sectional view taken generally along the line 14-14 from FIG. 13, and illustrates novel upper and lower shields of the present invention;

FIG. 15 is a chart of suitable shield materials for use in the present invention;

FIG. 16 is similar to FIG. 14, except that the shield is bent down over the sides of the microprocessor;

DETAILED DESCRIPTION OF THE INVENTION

Figure 1:
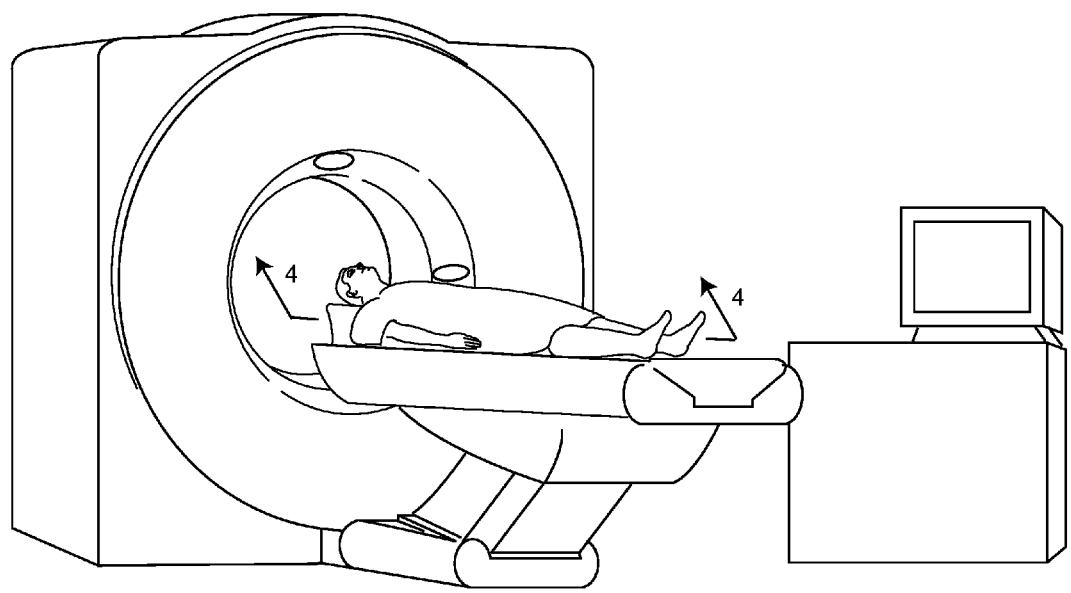
FIG. 1 is a pictorial view of a typical CT scan system.

As shown in the drawings, for purposes of illustration, the present invention relates to the protection of active implantable medical devices (AIMDs) from the undesirable effects that can be associated with ionizing radiation. Described are novel high atomic weight and high density shields which cooperate with body tissues such as skin, adipose, bone and muscle along with the housing of the AIMD to provide effective overall attenuation such that the X-ray intensity is reduced to the point where it does interfere with sensitive AIMD electronics. In a particularly preferred embodiment, the shield material is gold or similar material which has a much higher X-ray shielding co-efficient than lead.

As used herein, the term "computed tomography" (CT) will be used to describe any imaging modality utilizing ionizing radiation that involves computer reconstruction of 2 or 3D images from various cross-sectional slices taken at different angles. This would include X-ray computed tomography, positron emission tomography, single photon emission computed tomography, or any other modality using ionizing radiation.

Figure 2:
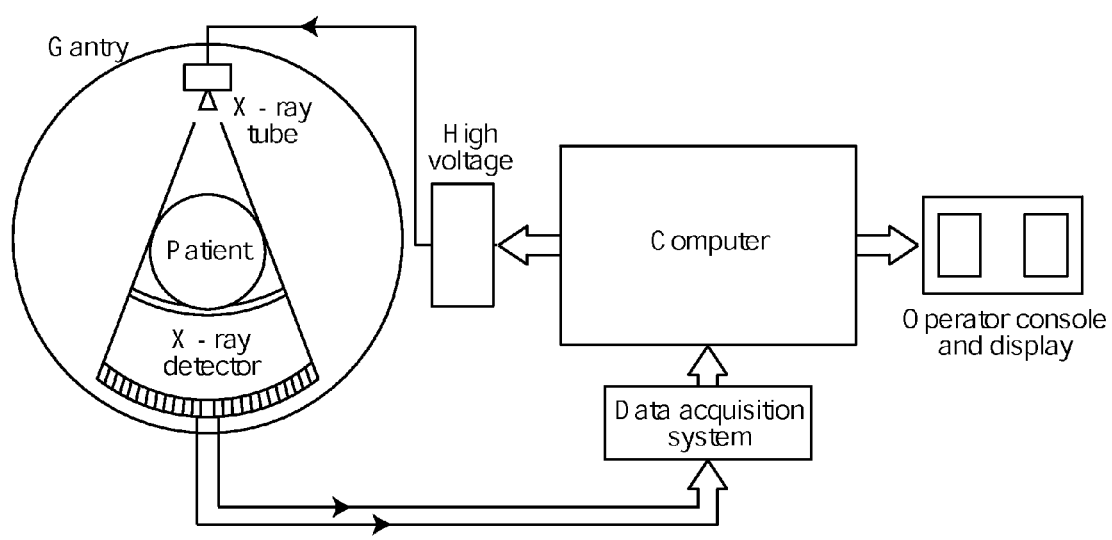
FIG. 2 is a block diagram explaining how CT scans work.

To better understand the construction, operation and use of CT scanning systems, reference is made to the accompanying FIGS. 1-6. FIG. 1 is a pictorial view of a typical CT scan system showing a patient about to be conveyed through the system, and FIG. 2 is a block diagram explaining how CT scans work. In general, the patient is placed inside a cylinder containing the X-ray source and an X-ray detector. In general, the X-ray source rotates about the patient (in some cases, the detectors rotate as well). A high-voltage source is connected to the X-ray tube or X-ray source. This is interfaced with a computer and an operator console. There is also a data acquisitions system that is fed from the X-ray detectors to the computer to build the images.

Figure 3:
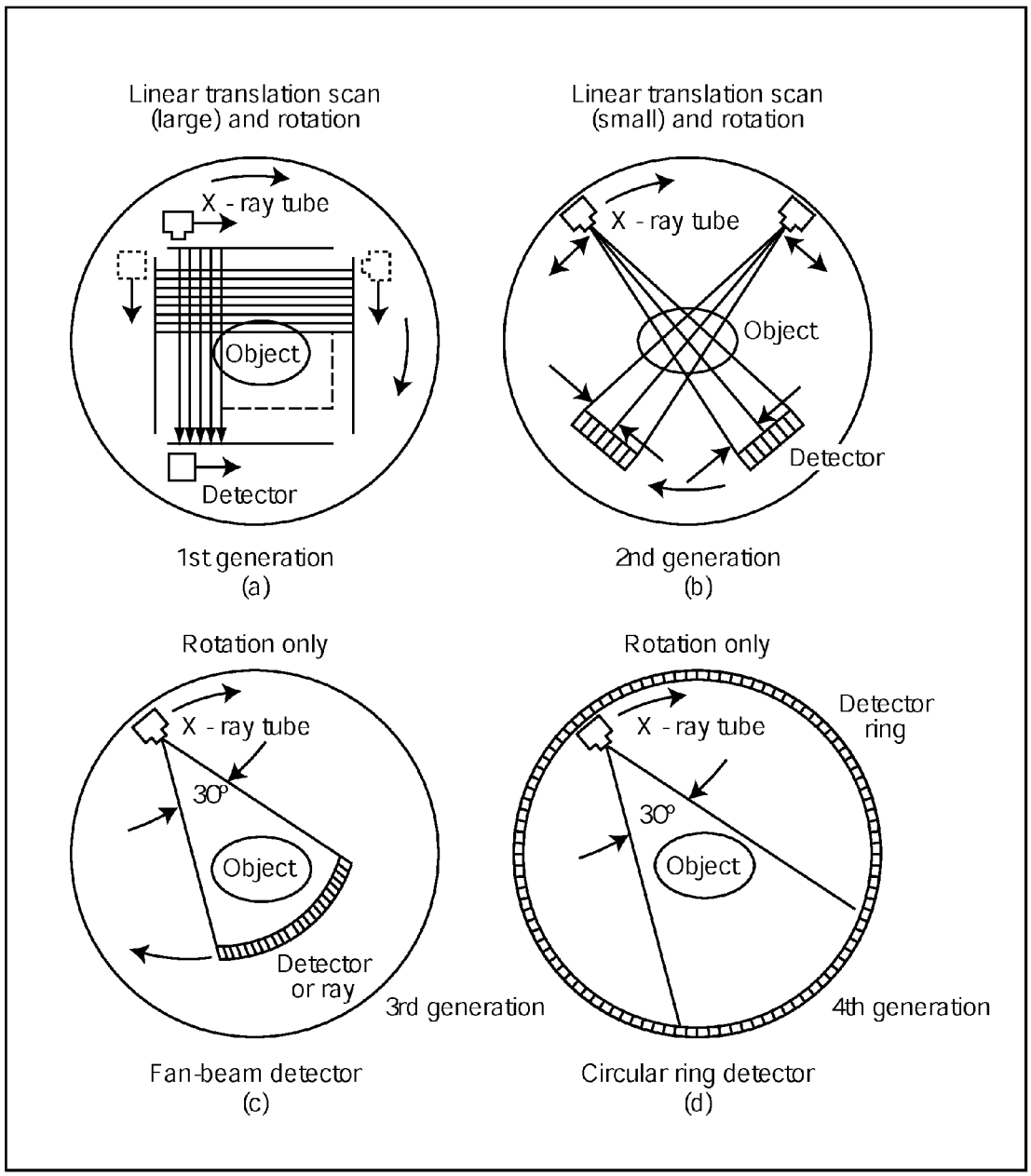
FIG. 3 illustrates various generations of CT scan systems.

FIG. 3 illustrates various generations of CT scan systems (reference book, Foundations of Medical Imaging by Cho et. al). First generation scanners were very crude in comparison to today's scanners. They used a linear translation scan (large) and rotation. Second generation machines incorporated a rotating X-ray tube along with an X-ray detector. Alignment in such systems and image quality was problematic. Third generation systems use a fan-beam X-ray source and rotating detector, which improves many of the image issues of the second generation. More modern (fourth generation) machines have a rotating X-ray source with a ring of stationary detectors which offers very high resolution and the ability to operate at very high dose rates. With the advent of sub-second rotation combined with multi-slice CT (up to 320-slices), high resolution and high speed can be obtained at the same time, allowing, for example, excellent imaging of the coronary arteries (cardiac CT angiography). However, as modern CT scanners have evolved, photon energies have increased as well as dose rate. As will be shown, this high dose rate radiation can be particularly problematic for the electronic circuits of AIMDs, such as cardiac pacemakers.

Figure 4:
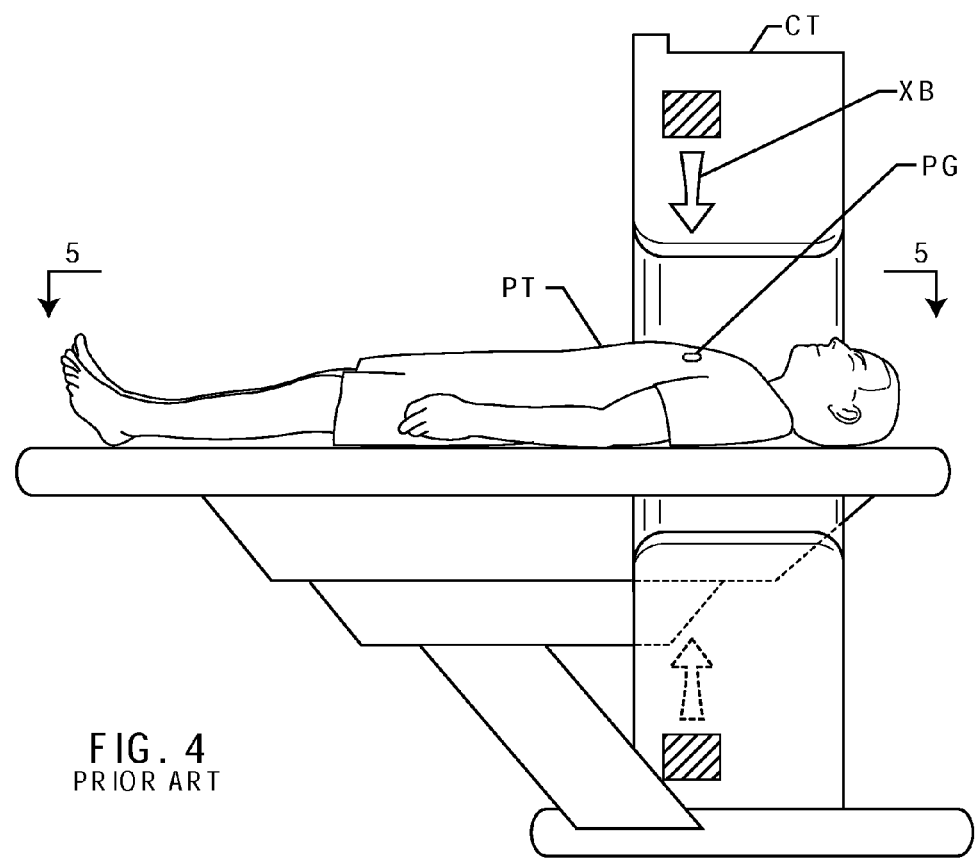
FIG. 4 is an elevational view taken generally along the line 4-4 from FIG. 1, showing a pacemaker patient within the CT scan system.

FIG. 4 is taken generally from section 4-4 from FIG. 1, and shows an AIMD patient PT (which in this case is a pacemaker patient) whereby the pacemaker PG is in the path of the rotating X-ray beam XB of the CT scanner CT. In this case, the patient's pacemaker PG is shown implanted just under the skin or pectoral muscle in a left-pectoral pocket. The X-ray source XB rotates at a gantry rate about the vertical plane.

Figure 5:
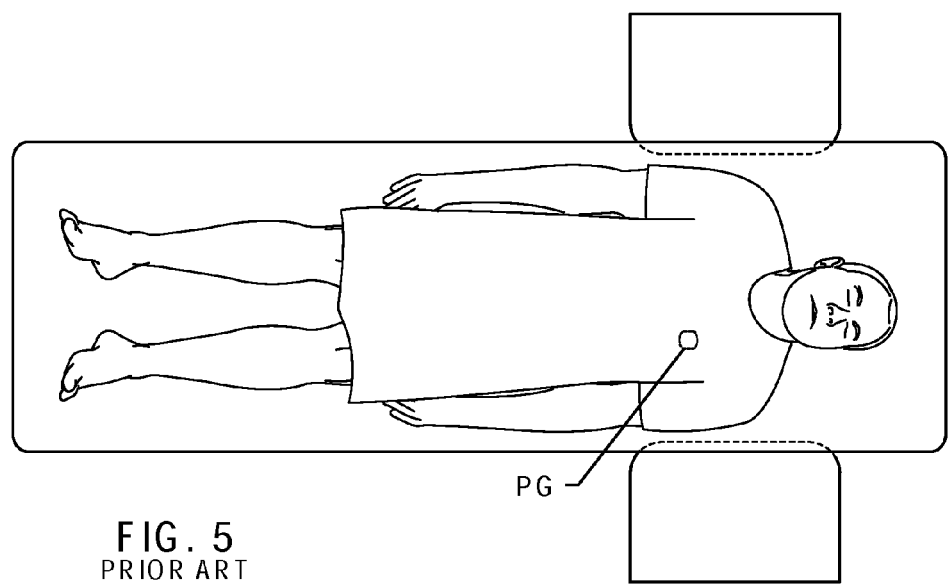
FIG. 5 is a top plan view of the pacemaker patient taken generally along the line 5-5 from FIG. 4.

FIG. 5 is a top view of the pacemaker patient PT taken generally from line 5-5 from FIG. 4. Shown is the pacemaker PG placed in a left pectoral pocket. Pacemakers are also often placed in a right pectoral pocket or other locations, such as the abdomen.

Figure 6:
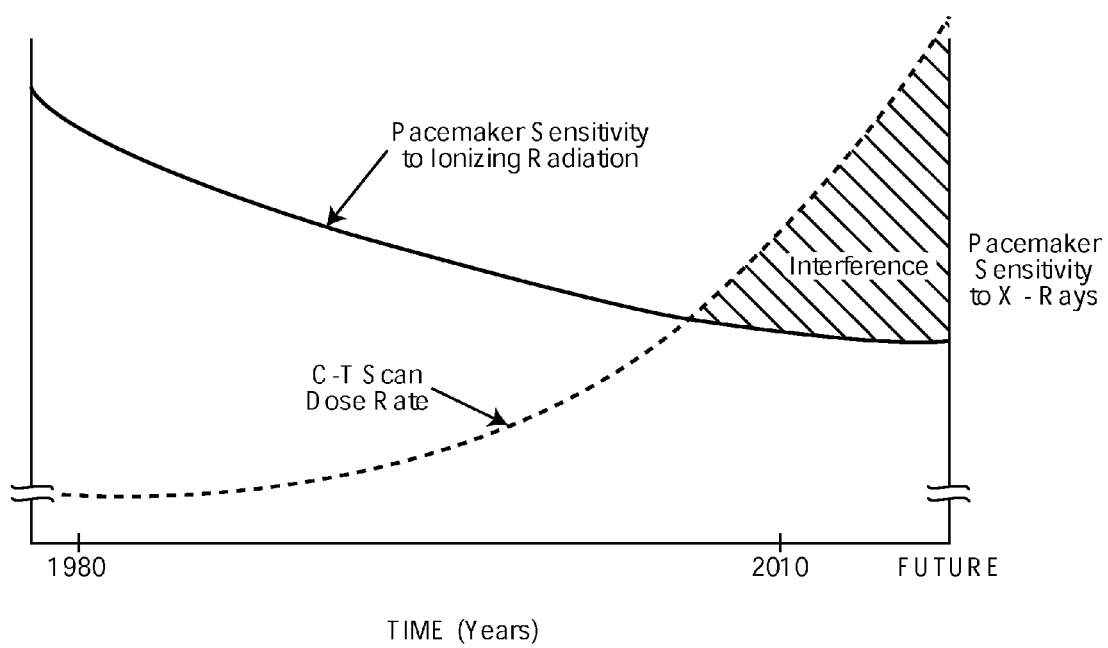
FIG. 6 is a notional drawing showing pacemaker sensitivity to ionizing radiation versus C-T scan dose rate over time.

FIG. 6 is a notional drawing showing two curves. The first curve is the CT scan dose rate over time. Old generation scanners (generation 1) had much lower radiation dose rates compared to some of the faster, modern scanners, such as those used for cardiac CT angiography. Accordingly, the CT dose rate and photon energies have been increasing over time. At the same time, in general, pacemakers have become more sensitive to ionizing radiation. One reason for this is that pacemaker microelectronic chip sets have continued to evolve to be smaller in size. Early model pacemakers were based on discrete transistors, which were quite large and had very robust P-N junctions. The early-model microchips, in comparison to modern chips, also had fewer P-N junctions. Another issue is the geometry of the transistor, such as gate length and width rather than just the thickness of the P-N junction. The P-N junction thickness is also determined by doping levels. Modern chip sets are submicron, which makes them highly volumetrically efficient. It also means they have less dynamic range and are generally more sensitive to large scale signals. In addition, they have a higher sensitivity to ionizing radiation.

In the past, it has been shown that microelectronic bit-flips due to radiation can cause either temporary or permanent effects including damage. A bit-flip might cause the AIMD to place itself in a mode that can cause damage, but at the transistor level, bit-flipping wouldn't directly cause damage. Damage is usually due to a complete latch up. In addition to CT scanners, there are other energetic X-ray sources that need to be considered, including cancer radiation treatments, real time fluoroscopy, and any other procedure that uses energetic X-rays. When the microelectronic circuits of an AIMD latch up, this becomes a very serious type of failure. Latch up typically involves high current drain from the onboard battery. Currents may be so high that circuits are damaged either directly or by heat effects. It is felt that incident radiation of a high dose rate causes current injection into circuits. Higher dose rates lead to higher induced currents. At some point, these currents become so high that interference or a malfunction of the device occurs.

For a cardiac pacemaker, over-sensing has been reported as well as changes in rate or even complete inhibition. For a pacemaker-dependent patient inhibition becomes an immediate, very life-threatening condition as there is a lack of heart beat. In the literature, cardiac pacemaker over-sensing has been tracked to the repetition rate of the X-ray source gantry of a CT scanner. This creates a pulse-type modulation (one report was at 120 Hz) which falls within the cardiac pacemaker sensing circuit pass band. If the pacemaker sees a pulse within its pass band, it will make a decision that it has a normal heart rate and then inhibit. This is a designed-in function that is designed to save battery life and prevent cardiac rate competition. It is highly undesirable to have an underlying intrinsic heart rate while at the same time having a competing second pulse at a different rate coming from a pacemaker; this can lead to dangerous arrhythmias. Many pacemaker patients are not dependent on their pacemaker all day long. Accordingly, when they have an intrinsic sinus rhythm, the pacemaker senses this and stops producing its pacing output.

Referring once again to FIG. 6, one can see that over time both the C-T scan dose rate and/or photon energies have been increasing. At the same time, pacemakers have become more sensitive to ionizing radiation. This leads to an increasing chance for interference to occur, such as pacemaker inhibition, rate competition and the like.

Figure 7:
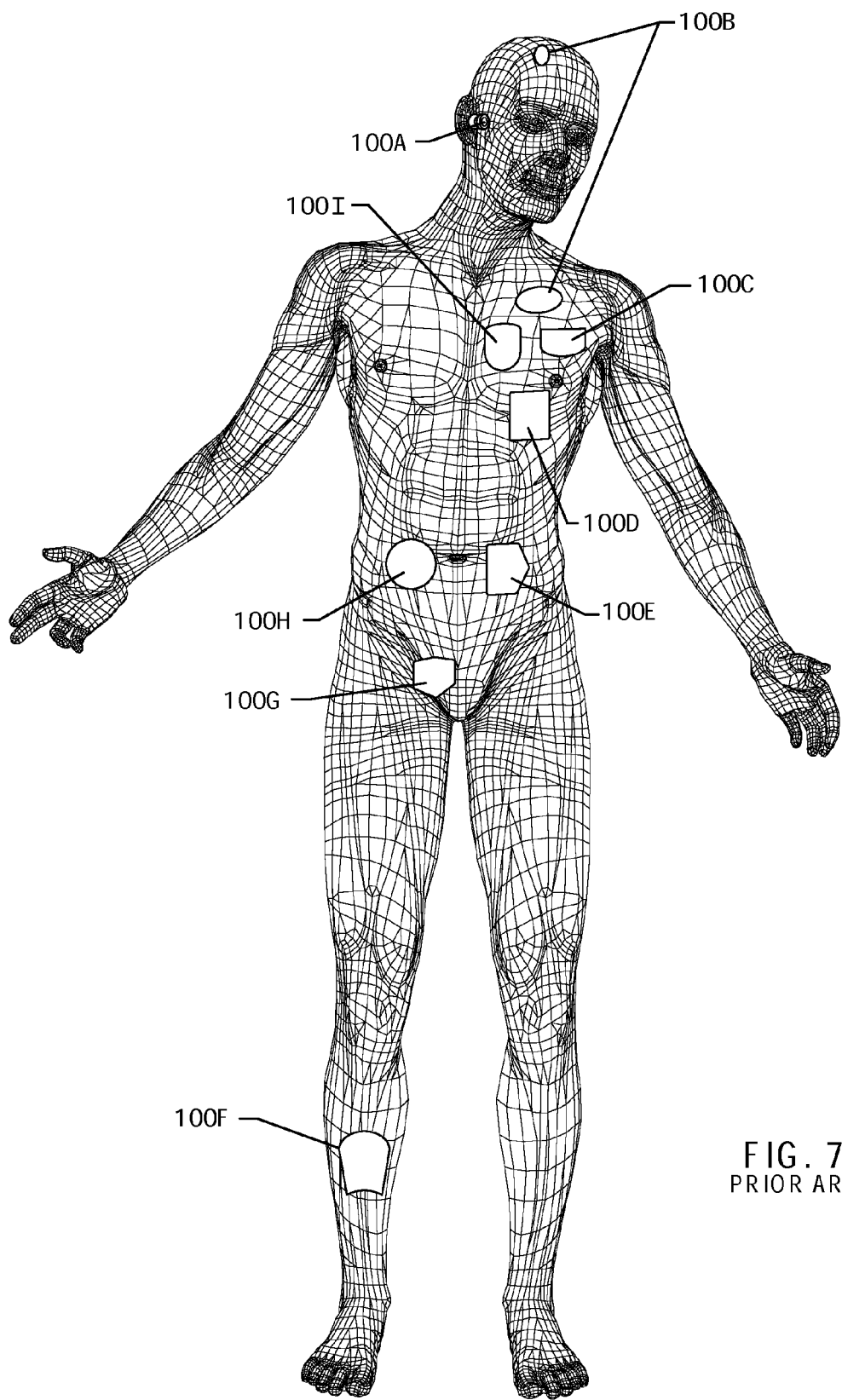
FIG. 7 illustrates placement within the human body of various types of active implantable medical devices (AIMDs)

FIG. 7 illustrates various types of active implantable medical devices that are currently in use and that may be affected by ionizing radiation. FIG. 7 is a wire frame model of a generic human body showing a number of implanted medical devices. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. 100C shows a cardiac pacemaker which is well-known in the art. 100D includes the family of left ventricular assist devices (LVAD's), and artificial hearts, including the artificial heart known as the Abiocor. 100E includes an entire family of drug pumps which can be used for dispensing of insulin, chemotherapy drugs, pain medications and the like. 100F includes a variety of bone growth stimulators for rapid healing of fractures. 100G includes urinary incontinence devices. 100H includes the family of pain relief spinal cord stimulators and anti-tremor stimulators. 100I includes a family of implantable cardioverter defibrillators (ICD) devices and also includes the family of congestive heart failure devices (CHF). This is also known in the art as cardiac resynchronization therapy devices, otherwise known as CRT devices.

The X-ray photon density that emerges from a homogenous absorber of thickness x, with energy $E_o$, and initial density $I_o$ may be expressed using Beer's Law as:

$$I = I_o e^{-\mu(\rho, Z, E_o)x}$$

Figure 8:
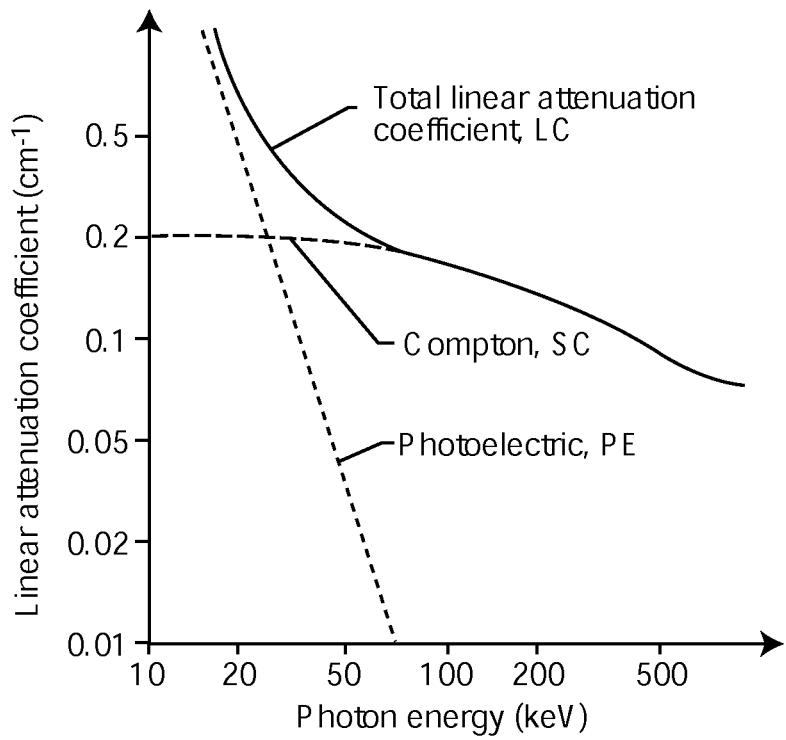
FIG. 8 is a chart showing that x-ray total attenuation co-efficient is the sum of two physical phenomena.

Here $\mu$ is the absorbing material's X-ray attenuation coefficient, which is a function of the absorber's density, atomic number, and the energy of the incident X-rays. As shown in FIG. 8, the X-ray total linear attenuation coefficient LC is the sum of two physical phenomena; the photoelectric effect PE, and the Compton scattering SC. For more information on this subject, one is referred to, *Foundations of Biomedical Imaging*, Wiley, New York, 1993, Z. Cho, J. Jones and M. Singh, the contents of which are incorporated herein. In photoelectric interactions an X-ray is completely absorbed and transfers all its energy to an electron. In Compton scattering X-rays are scattered, rather than absorbed, and undergo both a directional change and energy change. FIG. 8 depicts the interactions of X-rays in water and shows the individual contributions of each mechanism to the total linear attenuation coefficient.

Tables and graphs of the X-ray attenuation coefficient and the energy-attenuation coefficient have been compiled and published by the National Institute of Standards and Technology (NIST). One is directed to the work of J. H. Hubbell and S. M. Seltzer, found at: http:www.nist/gov/pml/data/xray-coef/index.cfm. The energy-attenuation coefficient tends to overestimate the attenuation of X-rays, whereas the attenuation coefficient tends to underestimate the attenuation of X-rays.

Figures 9, 10:
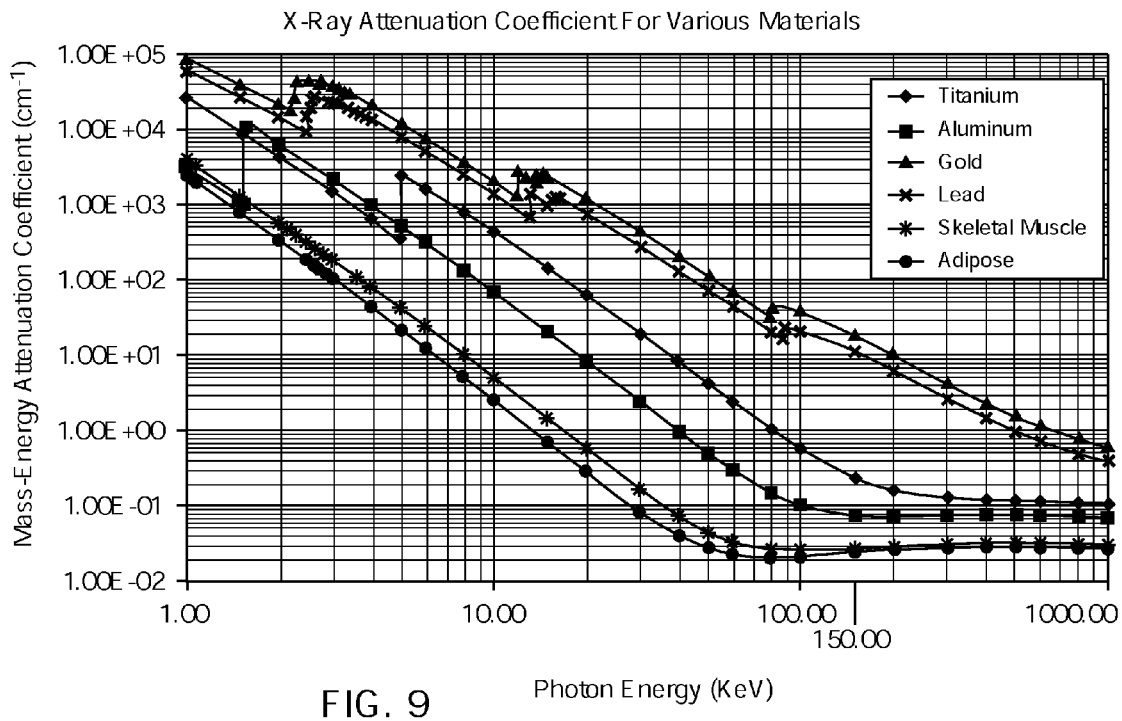
FIG. 9 is a chart showing energy-attenuation co-efficients for various materials.
FIG. 10 is a table showing half value layer (HVL) thicknesses for various materials plotted at a photon energy of 150 Key.

The energy-attenuation coefficient for various materials is shown in FIG. 9, where the data has been reorganized and reproduced from the NIST data.

For a typical CT scanner, the X-ray energy is taken to be equivalent to the voltage across the X-ray tube. Within the X-ray tube electrons are accelerated by the electric field created through the application of a large voltage placed from the tube's cathode to the tube's anode. This voltage is typically 70 KV for older CT scanners to as high as 140 KV for newer units. The kinetic energy of the electrons is equivalent to the tube voltage (i.e. a 70 KV tube voltage means 70 KeV electrons). These electrons collide with the anode material (typically tungsten, molybdenum, or copper), the product of which creates X-rays. Although it is not strictly true to assume that the X-ray energy is equivalent to the energy of the colliding electrons, hence the tube voltage (due to inefficiencies in the collision process that serve to lower the photon energy), it is difficult to estimate the true X-ray energy due to variations in generations or models of CT scanning equipment. Thus, equivalence between X-ray photon energy and tube voltage is assumed for ease of comparison. Furthermore, this assumption will result in more conservative estimates of shield absorber half value layer (HVL) thickness.

The first HVL thickness is the thickness required of a homogenous absorber to reduce the X-ray photon density, hence radiation dose rate, to 50 percent of the incident value. Solving Beer's Law above for $I/I_o=0.5$, the first HVL is equivalent to $-\ln(0.5)/\mu$. The second HVL reduces the photon density (and dose rate) to 25 percent, the third HVL to 12.5 percent, etc. FIG. 10 shows the HVLs for the materials plotted with a photon energy of 150 KeV identified.

As mentioned previously, the present invention relates to the protection of active implantable medical devices from the undesirable effects that can be associated with ionizing radiation.

Figure 11:
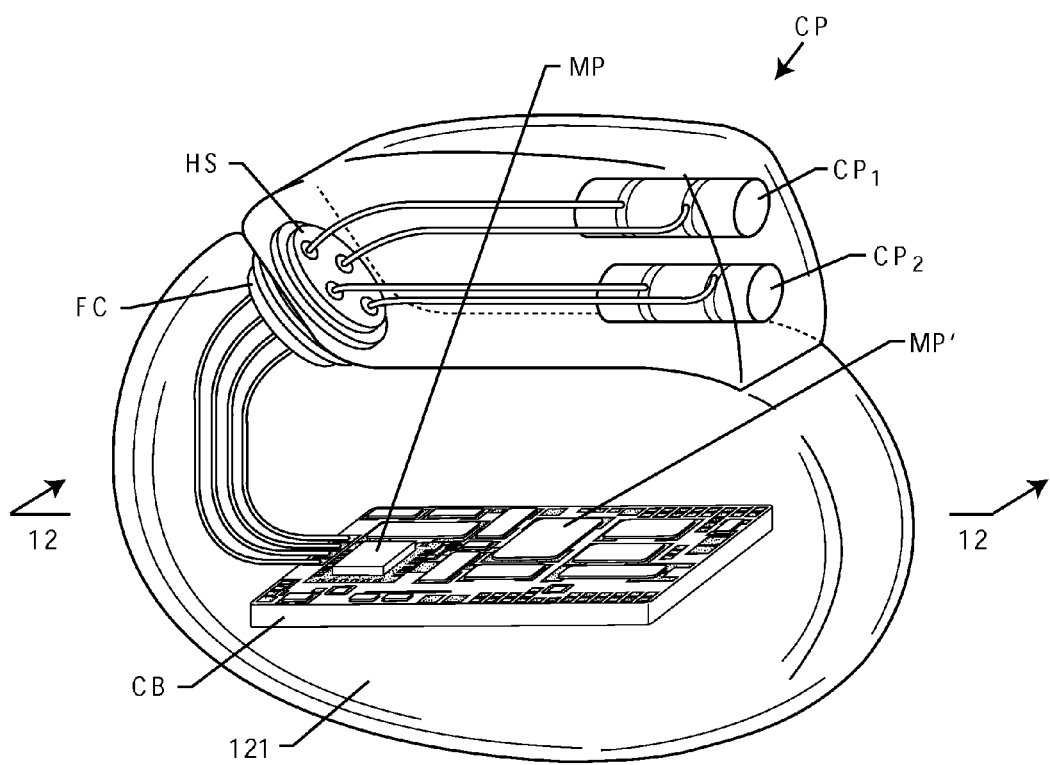
FIG. 11 is a perspective view of a typical prior art AIMD, such as a cardiac pacemaker.

The principle of the invention will be explained in connection with a typical prior art AIMD such as a cardiac pacemaker CP as illustrated in FIG. 11. One can see that it has dual chamber connector ports $CP_1$ and $CP_2$, which in this case, are designated by ISO Standard IS-1. These are routed to a hermetic terminal HS which has a co-bonded multipole EMI feedthrough capacitor FC attached to it. EMI filter capacitors are well known in the prior art. For example, see U.S. Pat. No. 5,333,095, the contents of which are incorporated herein by reference. These prior art EMI filters are very effective for attenuating electromagnetic interference that is induced on AIMD implanted leads or wiring. However, in the case of ionizing X-ray radiation, these prior art EMI filters have no effect. The type of interference that is reported from ionizing radiation sources is not electromagnetic interference. As defined herein, electromagnetic interference is that which would be wavelength dependent and coupled to implanted leads or conductors by means of antenna-like coupling. On the other hand, an X-ray radiation source directly penetrates through the thin conductive housing 121 of the AIMD (with little attenuation) and can directly induce currents into electronic circuits. The housing 121 is typically of titanium 0.010 to 0.025 inches thick. A particularly sensitive part of an AIMD electronic circuit board is one or more microprocessors MP. For example, in FIG. 11 a typical electronics package or circuit board CB is shown populated with one or more microprocessors MP, MP'.

Figure 12:
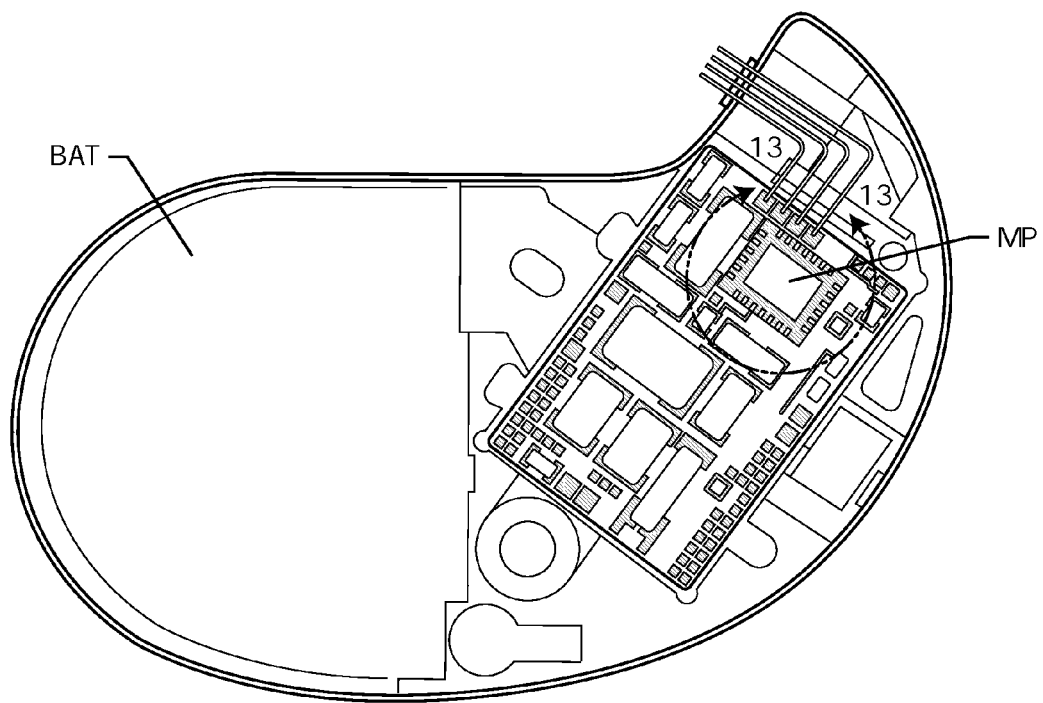
FIG. 12 is a sectional view through the AIMD of FIG. 11, taken generally along the line 12-12.

FIG. 12 is taken generally from section 12-12 from FIG. 11 with a focus on microprocessor MP. Microchips have very dense circuit packaging and tend to be the most susceptible to sources of ionizing radiation. The pacemaker battery BAT is also shown.

Figure 13:
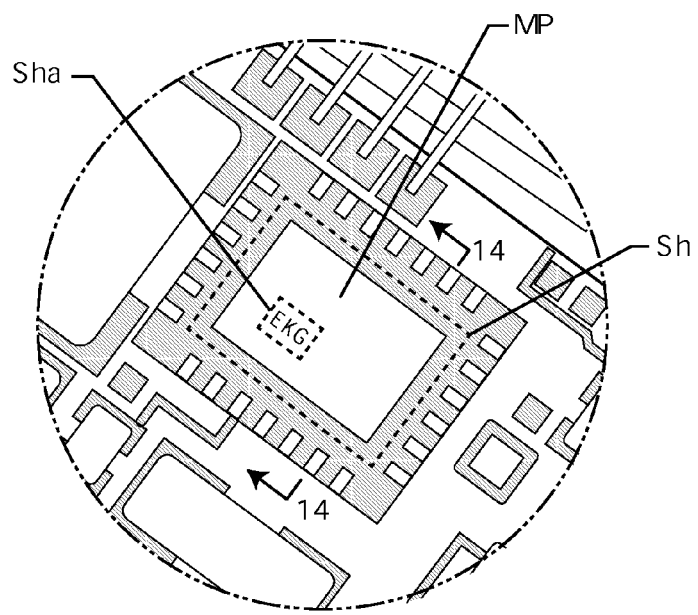
FIG. 13 is an enlarged view of the area of the microcircuit chip shown by line 13-13 from FIG. 12.

The microchip MP is shown blown up in FIG. 13 taken from section 13-13 from FIG. 12. The microchip MP is shown for illustrative purposes only. Typical microchips would have many more circuit interconnections and many more board layers than is presently illustrated.

FIG. 14 illustrates novel upper and lower shields $S_h$ and $S_h'$ of the present invention. These shields are designed to be very thin and very light-weight in accordance with the requirement for active implantable medical devices.

FIG. 15 is a list of suitable X-ray shield materials including atomic number, atomic weight and density. It is commonly known that lead is a very effective shield against ionizing radiation. As can be seen from FIG. 15, it has an atomic number of 82, an atomic weight of 207.2 and a density of 11.35 grams per cubic centimeter. What is not so well known is that tantalum, tungsten, iridium, platinum and gold all have similar atomic numbers, but much higher densities. Accordingly, they make even more effective ionizing radiation shields. Referring once again to FIG. 14, the shield material Sh is preferably made from any of the materials described in FIG. 15. It is shown bonded to the top of the microprocessor MP which is generally taken from section 14-14 from FIG. 13. Referring once again to FIG. 13, one can see the outline of the novel shield Sh shown as Sh Also shown in FIG. 13 is a smaller shield Sha This would be over the portion of the CMOS microprocessor known as the EKG amplifier. It has been shown that the EKG amplifier in cardiac pacemaker applications is particularly sensitive to the effect of high-dose rate ionizing radiation. Accordingly in an alternative embodiment, the shield Sh could be made much smaller as shown for shield Sha thereby saving volume, weight and cost.

Referring once again to FIG. 14, one can see that the ionizing radiation source XB is shown on the top of the unit. However, as previously described in FIGS. 1, 2 and 3, this ionizing radiation source XB revolves around the plane of the implanted device. Accordingly, shielding must also be provided on the bottom, shown as Sh'. In both cases, in FIG. 14, the shielding material is attached to an insulator surface IN which can be attached using a non-conductive thermal-setting material GP, GP'. In a preferred embodiment, a gold-backed foil or gold-backed film would have an adhesive and be easy to apply. It is not necessary that the X-ray shield Sh be conductive. For example, boron fiber composite materials that offer good X-ray shielding, mechanical strength and lightweight properties may be used. Both X-ray absorption and scattering can be achieved by such a composite shield. The addition of high-Z metal powders to a composite such as an epoxy can also provide X-ray shields. In order to be effective, all radiation must hit the high-Z material (gaps and holes in high-Z layers are not effective).

FIG. 16 is very similar to FIG. 14 except that the shield Sh is bent down over the sides of the microprocessor MP. This is in order to prevent edge radiation from penetrating into the microprocessor chip. One has to remember that the source of ionizing radiation is rotating 360 degrees about so that when the source is on the edge of FIG. 16, there is no shielding. Accordingly, bending the shield down of Sh, either with a rounded or square corner (not shown), is highly desirable. FIG. 16. also shows an alternative way of providing the bottom shield Sh'. In this case, the bottom shield is embedded within the microprocessor substrate and is shown as layer Sh". The details of the microprocessor substrate or AIMD circuit board are well known in the prior art and are therefore not detailed further herein.

Figure 17:
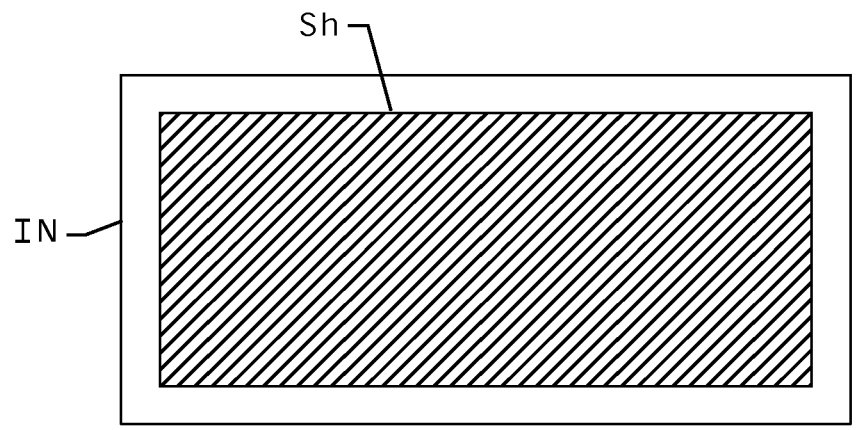
FIG. 17 is a top plan view taken generally along the line 17-17 from FIG. 14.

FIG. 17 is the top view of the shield Sh taken generally prom section 17-17 from FIG. 14.

Figure 18:
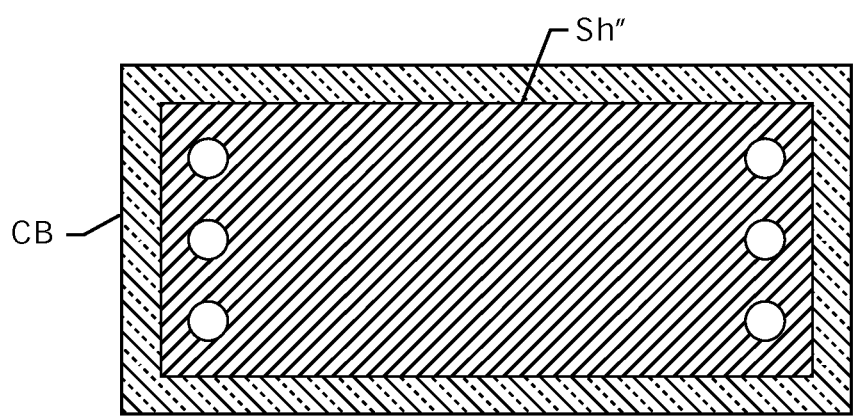
FIG. 18 is taken generally along the line 18-18 from FIG. 16.

FIG. 18 is taken from section 18-18 from FIG. 16 and shows the shield Sh" that is embedded within the substrate. The embedded bottom shield as illustrated in FIG. 18, would preferably be made of one of the materials as shown in FIG. 15. In other words, a traditional copper substrate or circuit trace could not be used. Copper does not have nearly a high enough atomic number or density for the purposes of the present invention.

Figure 19:
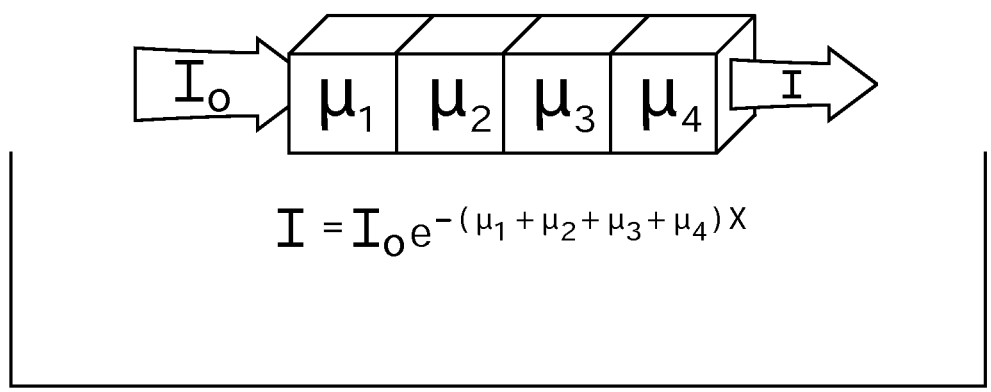
FIG. 19 is a schematic representation of an x-ray beam impinging on a multilayered structure.

FIG. 19 illustrates the case of an X-ray beam impinging on a multilayer structure where the layers have the same thickness. The total X-ray beam attenuation along this path (after taking logarithms) is the sum of the attenuation contributed by each block of material, $\mu_1$, $\mu_2$, $\mu_3$, and $\mu_4$.

The equation for the total attenuation is shown. In the case of a cardiac pacemaker with the X-ray gantry directed above the patient as shown in FIG. 4, $\mu_1$ would correspond to skin, $\mu_2$ would correspond to fat and muscle, $\mu_3$ would correspond to the housing of the AIMD (which is typically titanium or stainless steel), and $\mu_4$ would correspond to the novel microprocessor MP shield Sh as previously illustrated and described in FIGS. 13-18. Due to the high atomic number and density of the materials of the present invention as illustrated in FIG. 15, it will be shown that the bulk of the attenuation will come from the MP shield Sh (layer $\mu_4$).

An examination of the literature and the design of prior art pacemakers indicates that at least one Half Value Layer (HVL) thickness at 150 kilo electron volts is required. When one refers to FIG. 10, one can see that in order to achieve the first HVL it would take 281 millimeters of adipose or 238 millimeters of skeletal muscle. Of course, this is a ridiculously high number. Also the use of aluminum as used in space applications is not practical. 87.5 millimeters is over 3" of aluminum. However, when one examines gold, one can see that only 0.35 millimeters of gold shield Sh is required to achieve the first HVL. Accordingly, it becomes very practical for a pacemaker application to construct the shield materials Sh out of the materials listed in FIG. 15. Again, a comprehensive review of the literature indicates that 1 HVL would be sufficient to provide a high degree of attenuation and protection to most AIMDs. However, in order to account for future transient safety factors, the present invention is directed to HVLs between 0.5 and 10.

Referring once again to FIG. 19, the effects of adipose, skin and skeletal muscle cannot be completely discounted. This is because the literature has indicated that certain cardiac pacemakers have over-sensed at the Gantry rate of the CT ionizing radiation source. This would infer that the CMOS circuit is only sensitive when the X-ray beam is directly on top of the patient's chest where the adipose and muscle is the thinnest. In other words, the device is closest to the patient's skin surface in this orientation. When the X-ray beam is directed from the side or from the back, in certain cases, there does not seem to be any response from the implanted medical device. When one looks at a typical 150 kilovolt tube voltage, attenuating this by 50% (1 HVL) is further corroborated by the previous literature. In the literature, there are very few if any reports of 75 kilovolt CT scanners creating interference with implanted microprocessors such as the CMOS circuits of typical cardiac pacemakers. Accordingly, there is a significant amount of inferential evidence that 1 HVL will be sufficient and certainly within the range of 0.5-10 HVLs to provide for safety factor.

Figure 20:
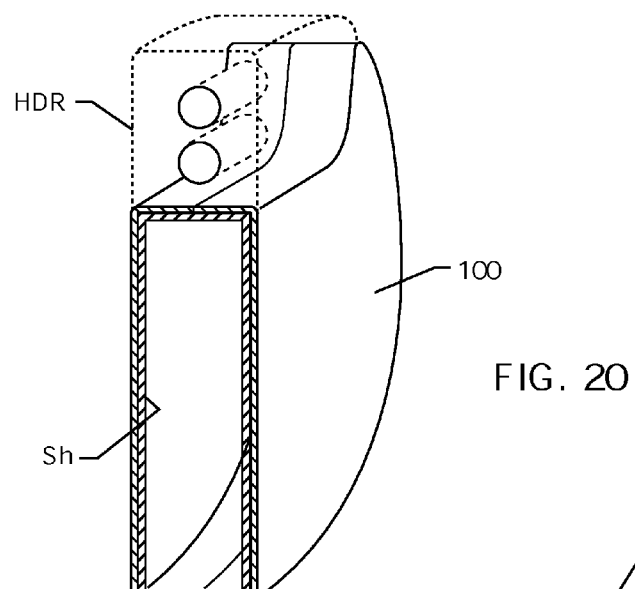
FIG. 20 is a cut-away view of a typical active implantable medical device housing.

FIG. 20 is a cut-away view of a typical active implantable medical device housing 100 with its header connector block HDR also shown in section. In this case, a high atomic weight and high density shielding material Sh, in accordance with the present invention, is used to coat the entire inside of the housing of the AIMD. This would, of course, provide attenuation to incident ionizing radiation in all orthogonal directions (x, y and z planes). However, coating the entire inside of the AIMD housing 100 with the shielding material would be expensive, take up considerable volume and also add weight to the device. Accordingly, this is a suitable technique, but it is not a preferred one.

Figure 21:
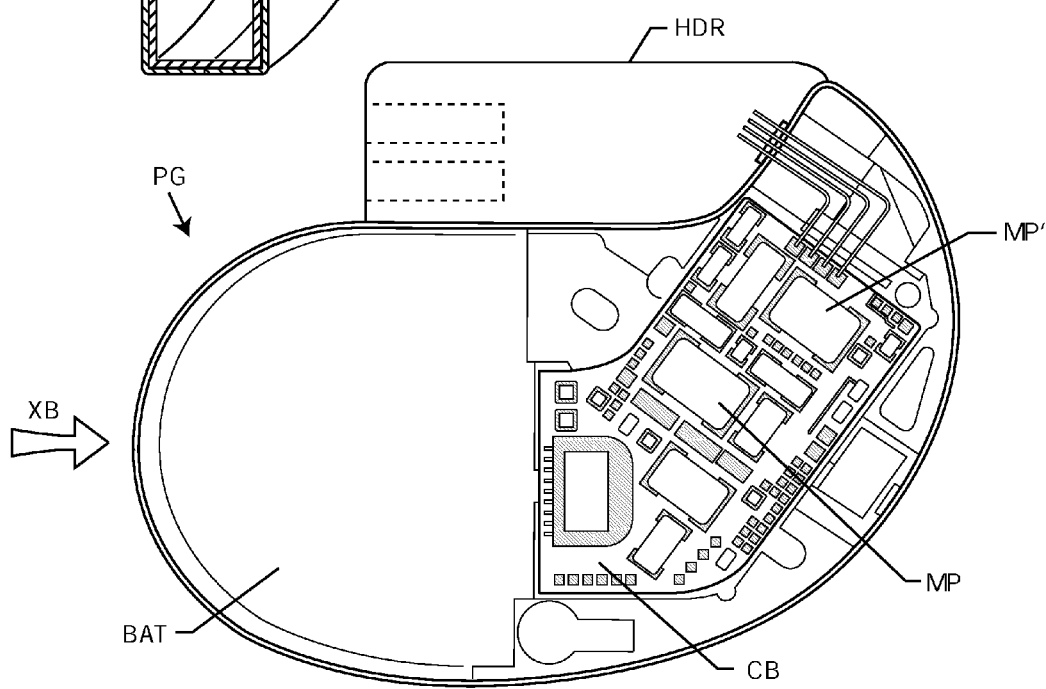
FIG. 21 is a sectional view of a typical AIMD, such as a cardiac pacemaker, showing its internal components.

FIG. 21 is an outline of a typical AIMD, such as a cardiac pacemaker PG, showing its internal long-life primary battery BAT, header block HDR and circuit substrate CB with microprocessor MP. A careful search of the literature indicates that tests of cardiac pacemakers with ionizing radiation sources indicate that they are much less sensitive to radiation when the ionizing radiation source XB comes from the direction of the battery. In other words, the battery (typically Lithium-ion) provides significant shielding against ionizing radiation. Batteries typically contain quite a bit of electrolyte and also metals such as lithium. In addition, the battery housings are made of titanium and stainless steel which also add to the total attenuation as shown in FIG. 19. Accordingly, it is a feature of the present invention to use the AIMD battery BAT as part of the shielding for AIMD microprocessors MP or MP' as shown.

Figure 22:
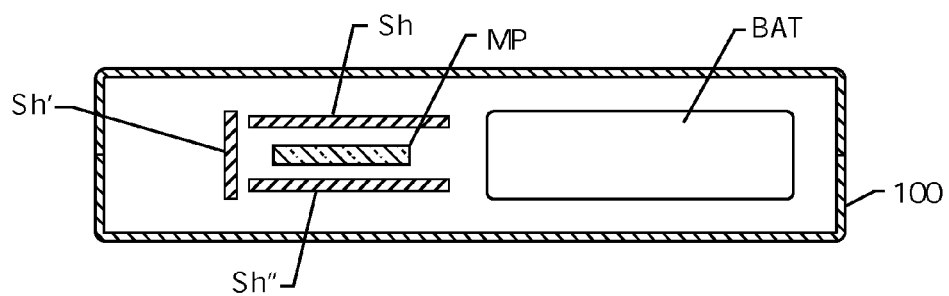
FIG. 22 is a schematic sectional view through the AIMD of FIG. 21 showing the arrangement of three ionizing radiation shields relative to the microprocessor and battery.

FIG. 22 is a general sectional view taken from FIG. 21 showing the microprocessor MP, the battery BAT and 3 shields Sh, Sh' and Sh". As one can see, the microprocessor is now protected from all incident X-ray planes.

Figure 23:
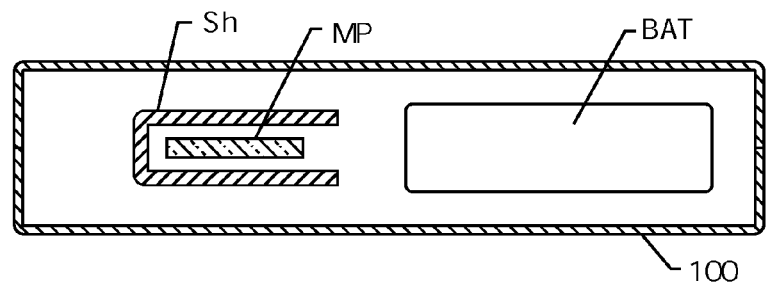
FIG. 23 is a view similar to FIG. 22 whereby the three shields have been integrated into one U-shaped shield extending around the microprocessor.

FIG. 23 is an improved version of FIG. 22 wherein the shield Sh forms a cup thereby protecting the microprocessor from all the other exposed planes except from the direction of the battery BAT.

Figure 24:
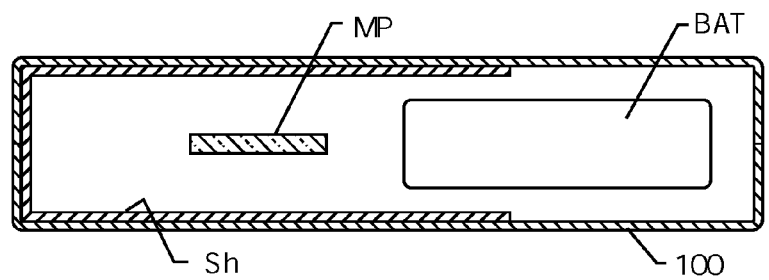
FIG. 24 is a view similar to FIGS. 22 and 23, showing an alternative methodology for protecting the microprocessor from ionizing radiation.

FIG. 24 is an alternative methodology where the battery BAT is used to shield the right-hand side of the AIMD housing wherein the inside of the AIMD housing has been coated with a suitable shielding material Sh as previously described in FIG. 20.

Figure 25:
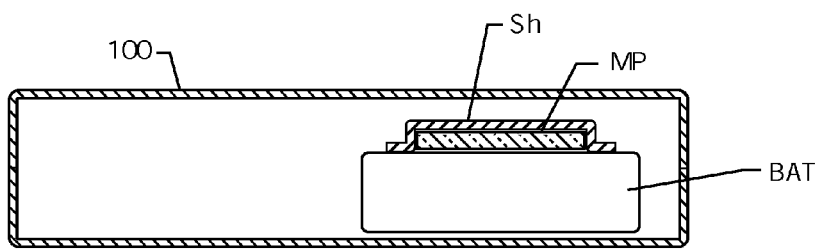
FIG. 25 is a view similar to FIGS. 22-24, illustrating yet another alternative configuration wherein the microprocessor is mounted directly on top of the battery and then a supplemental shield is placed over the microprocessor.

FIG. 25 is an alternate configuration wherein the microprocessor MP is mounted directly on top of the battery BAT and then a supplemental shield Sh in accordance with the present invention is placed over the microprocessor MP.

Figure 26:
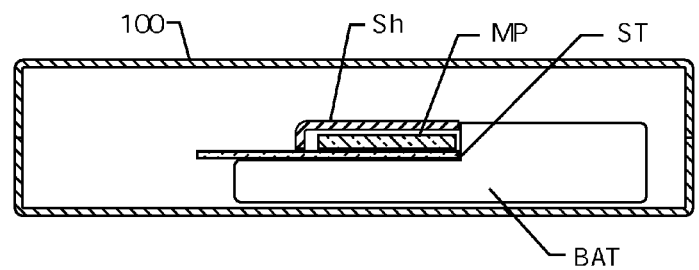
FIG. 26 is similar to FIG. 25 wherein the battery casing has a step in it wherein a portion of the microprocessor is seated therein.

FIG. 26 is another alternative where the battery casing MP has a step ST in it to partially or totally mount the microprocessor MP thereby providing additional shielding from both the x and y directions.

Figure 27:
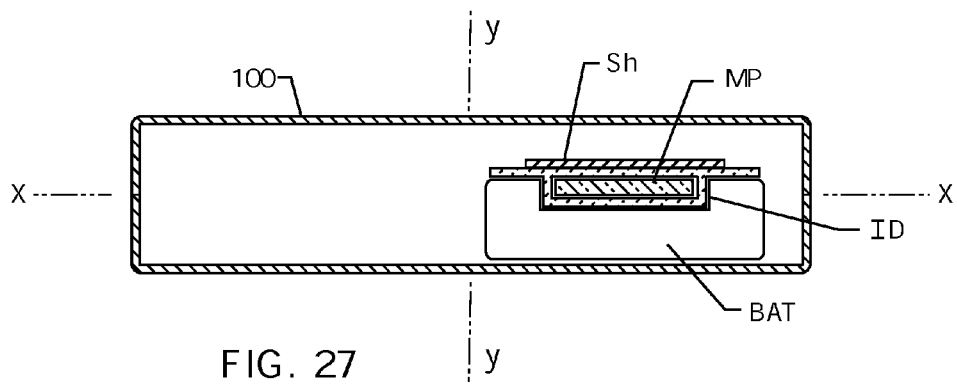
FIG. 27 is a view similar to FIGS. 25 and 26, showing full indentation of the battery in which the microprocessor is placed.

FIG. 27 shows a full indentation ID in the battery BAT into which the microprocessor MP is inserted so that only one shield $S_h$ is required to completely enclose and shield the microprocessor MP from all directions. Accordingly, as one can see, implantable device batteries can be modified with steps, notches or indentations in order to compliment the shielding of the microprocessor MP and thereby protect it from ionizing radiation sources.

Figure 28:
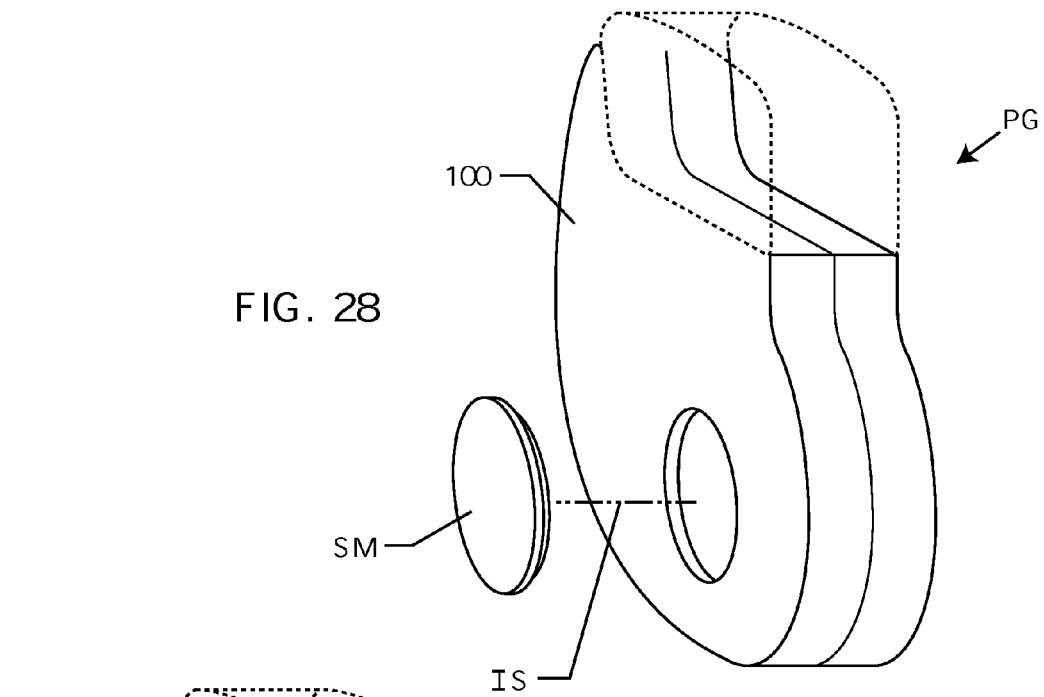
FIG. 28 illustrates a methodology of inserting a high atomic weight high density shield material into the housing to cover the internal microprocessor.

FIG. 28 illustrates a methodology of taking a typical titanium or stainless steel AIMD housing 100 and inserting IS a high atomic weight or co-bonded high atomic weight and high density shield material SM so that it covers an internal microprocessor MP (not shown) under that area of the housing.

Figure 29:
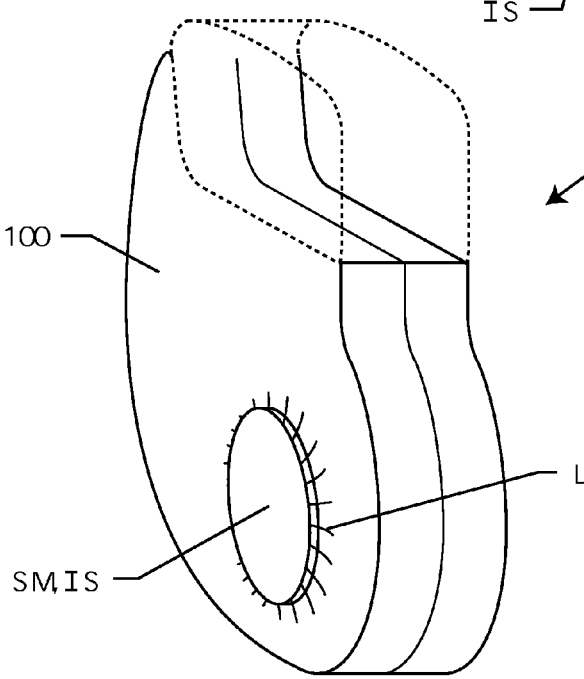
FIG. 29 is similar to FIG. 28, showing the shield insert laser welded into the housing.

FIG. 29 shows the shield insert IS laser welded LW into the housing 100 of the AIMD.

Figure 30:
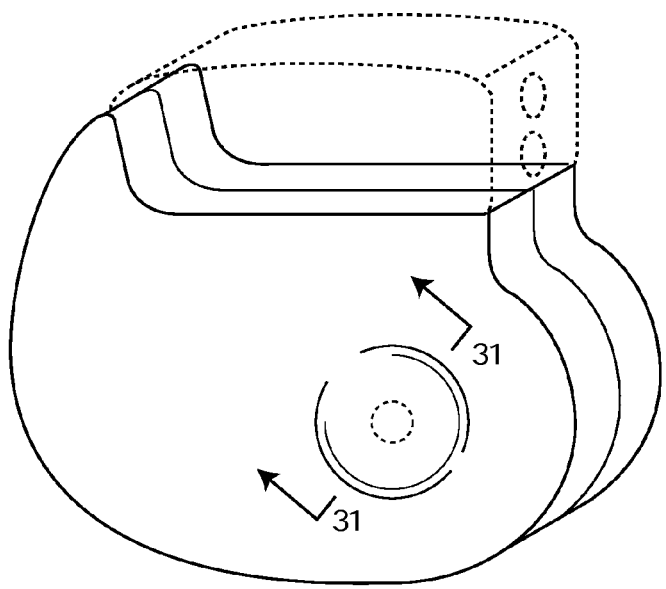
FIG. 30 is a front elevational view of the AIMD of FIG. 29, illustrating how the housing can be preformed to include a recess for accepting a shield therein.

FIG. 30 is a front view of the AIMD of FIG. 29.

Figure 31:
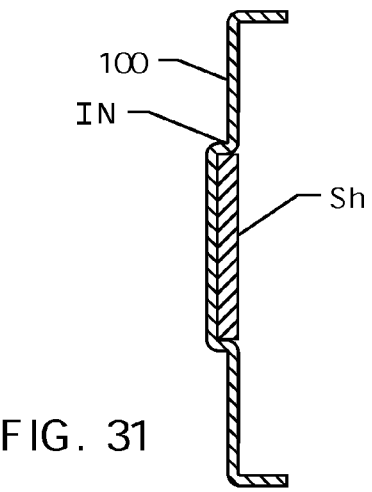
FIG. 31 is a sectional view taken generally along the line 31-31 from FIG. 30.

FIG. 31 is a taken from section 31-31 from FIG. 30 and shows an alternative methodology of inserting a high atomic weight and high density shield Sh into a stamped or machined indentation IN of the AIMD housing 100.

Figure 32:
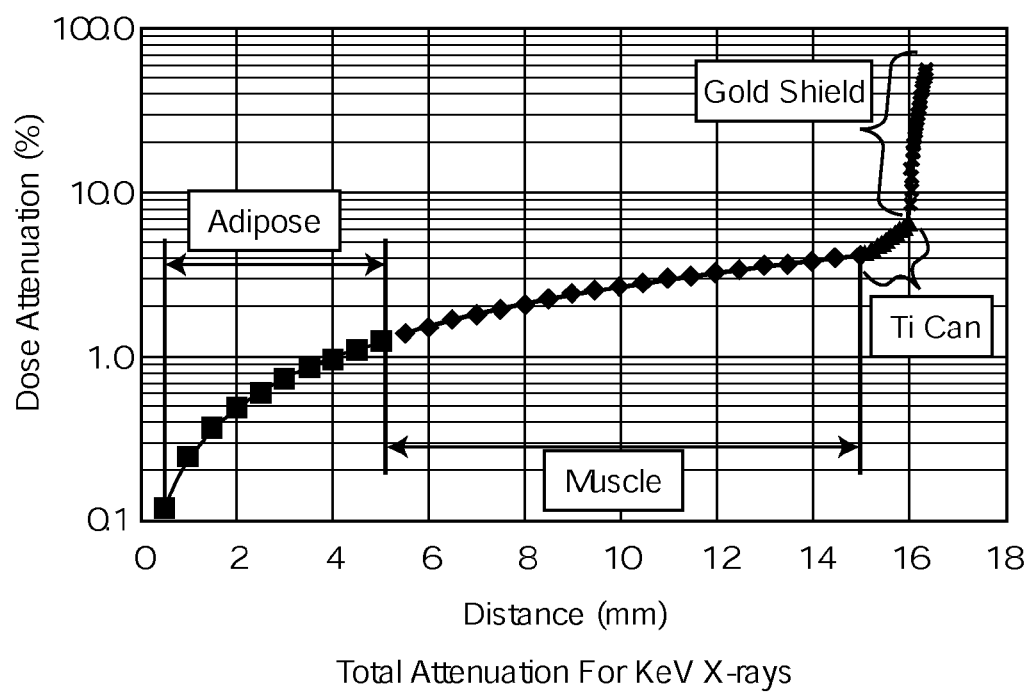
FIG. 32 is a graph illustrating total dose attenuation for KeV X-rays.

FIG. 32 demonstrates the total attenuation at 150 KeV for a multilayer structure consisting of 5 mm of adipose tissue, 10 mm of skeletal muscle, a pacemaker titanium can sidewall thickness of 1 mm, and a gold shield 0.38 mm thick (corresponding to 1 HVL). Although the tissue and pacemaker housing contribute a small amount of absorption, the bulk of the attenuation occurs in the gold layer.

In summary, there have been a number of very recent reports of high dose rate X-ray sources such as modern CT scanners interfering with implantable cardiac devices, including pacemakers and implantable cardioverter defibrillators. This, of course, is a very worrisome trend. Accordingly, what is described is a method of shielding and protecting the sensitive circuits of an active implantable medical device from the effects of ionizing radiation, such as that type of radiation that is commonly encountered during medical diagnostic or therapeutic procedures.

What is claimed is:

1. An ionizing radiation-protected active implantable medical device (AIMD), comprising:
   a) an AIMD housing;
   b) an electronics package including a microprocessor disposed within the AIMD housing, wherein the electronics package has a first external surface area and a remainder external surface area, which first and remainder external surface areas together add up to a total external surface area of the electronics package;
   c) a battery disposed within the AIMD housing, the battery being adapted to provide electrical power to the electronics package including the microprocessor, wherein the battery directly faces the first external surface area of the electronics package to thereby shield the first external surface area from ionizing radiation; and
   d) a gold shield disposed within the AIMD housing, wherein the gold shield is positioned between the AIMD housing and the remainder external surface area of the electronics package, but not between the battery and the AIMD housing to thereby provide an attenuation of ionizing radiation of at least 0.5 HVL at the remainder external surface area of the electronics package so that the battery together with the gold shield shields the total external surface area of the electronics package.

2. The medical device of claim 1, wherein the microprocessor includes CMOS circuits.

3. The medical device of claim 2, wherein the electronics package including the microprocessor comprises an EKG amplifier portion of a CMOS microprocessor.

4. The medical device of any of claims 1-3, wherein the gold shield comprises a plurality of gold shields.

5. The medical device of claim 4, wherein the plurality of gold shields positioned between the AIMD housing and the remainder external surface area of the electronics package substantially surround the electronics package except for the first external surface area facing the battery.

6. The medical device of claim 1, wherein the gold shield is attached to the electronics package.

7. The medical device of claim 1, wherein the gold shield includes an electrically insulated substrate adjacent to the remainder external surface area of the electronics package, and wherein a high density second shield is positioned adjacent to the electronics package opposite the gold shield.

8. The medical device of any of claims 1-3, wherein the remainder external surface area of the electronics package comprises a plurality of major external surfaces of the electronics package.

9. The medical device of claim 1, wherein the electronics package includes at least one of a circuit board and a substrate, and wherein the gold shield is disposed intermediate the AIMD housing and on or within at least one of the circuit board and the substrate.

10. The medical device of claim 1, wherein the AIMD is selected from the group consisting of a cochlear implant, a piezoelectric sound bridge transducer, a neurostimulator, a brain stimulator, a cardiac pacemaker, a left ventricular assist device, an artificial heart, a drug pump, a bone-growth stimulator, a urinary incontinence device, a pain relief spinal, cord stimulator, an anti-tremor stimulator, an implantable cardioverter defibrillator, and a congestive heart failure device.

11. The medical device of claim 1, wherein the cold shield is a liner contacted to an interior surface of the AIMD housing.

12. The medical device of claim 11, wherein the gold shield is plated over a portion of the interior surface of the AIMD housing.

13. The medical device of claim 1 wherein the AIMD housing includes an interior recess in which the gold shield is disposed.

14. The medical device of claim 1, wherein the gold shield has a thickness of at least 0.25 millimeters.

15. The medical device of claim 1 wherein the gold shield is co-bonded to a biocompatible substrate disposed within the AIMD housing.

16. The medical device of claim 1 wherein the gold shield has a thickness of from 0.25 millimeters to 1.05 millimeters.

17. The medical device of claim 1 wherein the AIMD housing is of titanium.

18. An ionizing radiation-protected active implantable medical device (AIMD), comprising:
   a) an AIMD housing;
   b) an electronics package within the AIMD housing, wherein the electronics package has a first external surface area and a remainder external surface area, which first and remainder external surface areas add up to a total external surface area of the electronics package;
   c) a battery disposed within the AIMD housing, the battery being adapted to provide electrical power to the electronics package including the microprocessor, wherein the battery directly faces the first external surface area of the electronics package to thereby shield the first external surface area from ionizing radiation; and
   d) an ionizing radiation shield disposed within the AIMD housing and being of a metal selected from the group consisting of gold, platinum, iridium, tungsten and tantalum, wherein the ionizing radiation shield is disposed between the AIMD housing and the remainder external, surface area of the electronics package, but not between the battery and the AIMD housing to thereby provide an attenuation of ionizing radiation of at least 0.5 HVL at the remainder external surface area of the electronics package so that the battery together with the ionizing radiation shield shields the total external surface area of electronics package.

19. The medical device of claim 18, wherein the ionizing radiation shield is adapted to be disposed over an EKG amplifier portion of a CMOS microprocessor comprising the electronics package.

20. The medical device of claim 18, wherein the ionizing radiation shield is a liner contacted to an interior surface of the AIMD housing.

21. The medical device of claim 18 wherein the ionizing radiation shield is plated over a portion of the interior surface of the AIMD housing.

22. The medical device of claim 18 wherein the AIMD housing includes an interior recess in which the ionizing radiation shield is disposed.

23. The medical device of claim 18 wherein the ionizing radiation shield has a thickness of at least 0.25 millimeters.

24. The medical device of claim 18 wherein the ionizing radiation shield comprises a plurality of shields positioned between the AIMD housing and the remainder external surface area of the electronics package to thereby substantially surrounding the electronic package except for the first external surface area facing the battery.

25. The medical device of claim 18 wherein the ionizing radiation shield is attached to the electronics package.

26. The medical device of claim 18 wherein the remainder external surface area of the electronics package comprises a plurality of major surfaces of the electronics package.

27. The medical device of claim 18 wherein the ionizing radiation shield includes an electrically insulated substrate adjacent to the remainder external surface area of the electronics package, and wherein a high density second shield is positioned adjacent to the electronics package opposite the ionizing radiation shield.

28. The medical device of claim 18 wherein the electronics package includes a circuit board, and wherein the ionizing radiation shield is disposed on or within the circuit board.

29. The medical device of claim 18 wherein the AIMD is selected from the group consisting of a cochlear implant, a piezoelectric sound bridge transducer, a neurostimulator, a brain stimulator, a cardiac pacemaker, a left ventricular assist device, an artificial heart, a drug pump, a bone growth stimulator, a urinary incontinence device, a pain relief spinal cord stimulator, an anti-tremor stimulator, an implantable cardioverter defibrillator, and a congestive heart failure device.

30. The medical device of claim 18 wherein the ionizing radiation shield is co-bonded to a biocompatible substrate disposed within the AIMD housing.

31. The medical device of claim 18 wherein the ionizing radiation shield has a thickness of from 0.25 millimeters to 1.05 millimeters.

32. The medical device of claim 18 wherein the electronics package within the AIMD housing includes a CMOS microprocessor.

33. The medical device of claim 18 wherein the AIMD housing is of titanium.

34. An ionizing radiation-protected active implantable medical device (AIMD), comprising:
a) an AIMD housing;
b) an electronics package within the AIMD housing, wherein the electronics package has a first external surface area and a remainder external surface area, which first and remainder external surface areas add up to a total external surface area of the electronics package;
c) a battery disposed within the AIMD housing, the battery being adapted to provide electrical power to the electronics package including the microprocessor, wherein the battery directly faces the first external surface area of the electronics package to thereby shield the first external surface area from ionizing radiation; and
d) a gold shield having a thickness of at least 0.25 millimeters disposed within the AIMD housing, wherein the gold shield is positioned between the AIMD housing and the remainder external surface area of the electronics package, but not between the battery and the AIMD housing to thereby provide a shielded portion at the remainder external surface area of the electronics package so that the battery together with the gold shield shields the total external surface area of the electronics package.

35. The medical device of claim 34, wherein the gold shield is a liner disposed adjacent to an interior surface of the AIMD housing.

36. The medical device of claim 35, wherein the gold shield is plated over a portion of the interior surface of the AIMD housing.

37. The medical device of claim 35 wherein the AIMD housing includes an interior recess in which the gold shield is disposed.

38. The medical device of claim 34, wherein the gold shield comprises a plurality of gold shields substantially surrounding the electronic package except for the first external surface area facing the battery.

39. The medical device of claim 34, wherein the gold shield is attached to the electronics package.

40. The medical device of claim 34 or 39, wherein the remainder external surface area of the electronics package comprises a plurality of major surfaces of the electronics package.

41. The medical device of claim 34, wherein the gold shield includes an electrically insulated substrate adjacent to the remainder external surface area of the electronics package, and wherein a high density second shield is positioned adjacent to the electronics package opposite the gold shield.

42. The medical device of claim 34, wherein the electronics package includes at least one of a circuit board and a substrate, and wherein the gold shield is disposed intermediate the AIMD housing and on or within the at least one of the circuit board and the substrate.

43. The medical device of claim 34, wherein the AIMD is selected from the group consisting of a cochlear implant, a piezoelectric sound bridge transducer, a neurostimulator, a brain stimulator, a cardiac pacemaker, a left ventricular assist device, an artificial heart, a drug pump, a bone growth stimulator, a urinary incontinence device, a pain relief spinal cord stimulator, an anti-tremor stimulator, an implantable cardioverter defibrillator, and a congestive heart failure device.

44. The medical device of claim 34 wherein the cold shield is co-bonded to a biocompatible substrate disposed within the AIMD housing.

45. The medical, device of claim 34 wherein the cold shield has a thickness of from 0.25 millimeters to 1.05 millimeters.

46. The medical device of claim 34 wherein the gold shield provides an attenuation of ionizing radiation of at least 0.5 HVL.

* * * * *

UNITED STATES PATENT AND TRADEMARK OFFICE
CERTIFICATE OF CORRECTION

PATENT NO. : 8,694,102 B2
APPLICATION NO. : 13/367501
DATED : April 8, 2014
INVENTOR(S) : Ryan A. Stevenson et al.

Page 1 of 1

It is certified that error appears in the above-identified patent and that said Letters Patent is hereby corrected as shown below:

In the Claims

Column 18, line 27 (Claim 10, line 6) after the word "spinal" delete the ","

Column 18, line 66 (Claim 18, line 19) after the word "external" delete the ","

Column 20, line 57 (Claim 44, line 1) delete "cold" and insert --gold--

Column 20, line 60 (Claim 45, line 1) delete "cold" and insert --gold--

Signed and Sealed this
Twenty-third Day of September, 2014

Michelle K. Lee
*Deputy Director of the United States Patent and Trademark Office*